United States Patent

Soenksen et al.

[11] Patent Number: 5,995,645
[45] Date of Patent: *Nov. 30, 1999

[54] METHOD OF CANCER CELL DETECTION

[75] Inventors: Dirk C. Soenksen; George McNamara, both of Carlsbad, Calif.; Yuval Garini, Koranit; Nir Katzir, Givat Elah, both of Israel

[73] Assignee: Applied Spectral Imaging Ltd., Migdal Haemek, Israel

[*] Notice: This patent is subject to a terminal disclaimer.

[21] Appl. No.: 08/984,990

[22] Filed: Dec. 4, 1997

[51] Int. Cl.[6] ............ G06K 9/00; G01N 33/574; G01N 33/48; G01J 3/28
[52] U.S. Cl. ............ 382/133; 356/328; 356/346; 435/7.23; 436/63
[58] Field of Search ............ 382/128, 133; 356/326, 328, 345, 346; 435/6, 7.23; 436/63, 141, 171, 183

[56] References Cited

U.S. PATENT DOCUMENTS

| | | | |
|---|---|---|---|
| 4,085,006 | 4/1978 | Mindick et al. | 435/35 |
| 4,426,525 | 1/1984 | Hezumi et al. | 546/22 |
| 4,581,223 | 4/1986 | Kass | 435/34 |
| 4,622,291 | 11/1986 | Picciolo et al. | 435/4 |
| 4,721,669 | 1/1988 | Barton | 435/6 |
| 4,859,584 | 8/1989 | Horan et al. | 435/29 |
| 4,998,284 | 3/1991 | Bacus et al. | 382/133 |
| 5,093,106 | 3/1992 | Dzbanovsky et al. | 424/9.6 |
| 5,106,744 | 4/1992 | Kass | 435/29 |
| 5,109,429 | 4/1992 | Bacus et al. | 436/183 |
| 5,149,527 | 9/1992 | Weisenthal | 424/85.2 |
| 5,194,373 | 3/1993 | Williams et al. | 435/39 |
| 5,377,003 | 12/1994 | Lewis et al. | 356/346 |
| 5,539,517 | 7/1996 | Cabib et al. | 356/346 |
| 5,784,162 | 7/1998 | Cabib et al. | 356/346 |
| 5,817,462 | 10/1998 | Garini et al. | 435/6 |

*Primary Examiner*—Jon Chang
*Assistant Examiner*—Mehrdad Dastouri
*Attorney, Agent, or Firm*—Mark M. Friedman

[57] ABSTRACT

A method for cancer cell detection including the steps of (a) staining an analyzed sample with at least first and second dyes, the dyes being selected such that the first dye better adheres to normal cells whereas the second dye better adheres to cancer cells; (b) spectrally imaging the sample through an optical device being optically connected to an imaging spectrometer thereby obtaining a spectrum of each pixel of the sample; (c) based on the spectra, evaluating concentrations of the first and second dyes for each of the pixels; and (d) based on the concentrations detecting the presence of cancer cells in the sample.

20 Claims, 10 Drawing Sheets

METHOD OF CANCER CELL DETECTION

FIELD AND BACKGROUND OF THE INVENTION

The present invention relates to spectral methods in general and, more particularly, to spectral imaging methods for cancer cell detection. The method of the present invention is based upon new analysis approach of old cell staining procedures. In particular the method of the present invention is based upon determination of a ratio between two dyes used to stain cells and a presentation of the results in a meaningful way. Apparently, cancer and non-cancer cells present different ratios and therefore the method is applicable for cancer cell detection.

A spectrometer is an apparatus designed to accept light, to separate (disperse) it into its component wavelengths, and measure the lights spectrum, that is the intensity of the light as a function of its wavelength. An imaging spectrometer is one that collects incident light from a scene and measures the spectra of each pixel (i.e., picture element) thereof.

Spectroscopy is a well known analytical tool which has been used for decades in science and industry to characterize materials and processes based on the spectral signatures of chemical constituents. The physical basis of spectroscopy is the interaction of light with matter. Traditionally, spectroscopy is the measurement of the light intensity emitted, transmitted, scattered or reflected from a sample, as a function of wavelength, at high spectral resolution, but without any spatial information.

Spectral imaging, on the other hand, is a combination of high resolution spectroscopy and high resolution imaging (i.e., spatial information). Most of the works so far described concern either obtaining high spatial resolution information from a biological sample yet providing only limited spectral information, for example, when high spatial resolution imaging is performed with one or several discrete band-pass filters [See, Andersson-Engels et al. (1990) Proceedings of SPIE—Bioimaging and Two-Dimensional Spectroscopy, 1205, pp. 179–189], or alternatively, obtaining high spectral resolution (e.g., a full spectrum), yet limited in spatial resolution to a small number of points of the sample or averaged over the whole sample [See for example, U.S. Pat. No. 4,930,516, to Alfano et al.].

Conceptually, a spectral bio-imaging system consists of (i) a measurement system, and (ii) an analysis software. The measurement system includes all of the optics, electronics and the manner in which the sample is illuminated (e.g., light source selection), the mode of measurement (e.g., fluorescence or transmission), as well as the calibration best suited for extracting the desired results from the measurement. The analysis software includes all of the software and mathematical algorithms necessary to analyze and display important results in a meaningful way.

Spectral imaging has been used for decades in the area of remote sensing to provide important insights in the study of Earth and other planets by identifying characteristic spectral absorption features. However, the high cost, size and configuration of remote sensing spectral imaging systems (e.g., Landsat, AVIRIS) has limited their use to air and satellite-born applications [See, Maymon and Neeck (1988) Proceedings of SPIE—Recent Advances in Sensors, Radiometry and Data Processing for Remote Sensing, 924, pp. 10–22; Dozier (1988) Proceedings of SPIE—Recent Advances in Sensors, Radiometry and Data Processing for Remote Sensing, 924, pp. 23–30].

There are three basic types of spectral dispersion methods that might be considered for a spectral bio-imaging system: (i) spectral grating or prism, (ii) spectral filters and (iii) interferometric spectroscopy. As will be described below, the latter is best suited to implement the method of the present invention, yet as will be appreciated by one ordinarily skilled in the art, grating, prism and filters based spectral bio-imaging systems may also be found useful.

In a grating or prism (i.e., monochromator) based systems, also known as slit-type imaging spectrometers, such as for example the DILOR system: [see, Valisa et al. (September 1995) presentation at the SPIE Conference European Medical Optics Week, BiOS Europe '95, Barcelona, Spain], only one axis of a CCD (charge coupled device) array detector (the spatial axis) provides real imagery data, while a second (spectral) axis is used for sampling the intensity of the light which is dispersed by the grating or prism as function of wavelength. The system also has a slit in a first focal plane, limiting the field of view at any given time to a line of pixels. Therefore, a full image can only be obtained after scanning the grating (or prism) or the incoming beam in a direction parallel to the spectral axis of the CCD in a method known in the literature as line scanning. The inability to visualize the two-dimensional image before the whole measurement is completed, makes it impossible to choose, prior to making the measurement, a desired region of interest from within the field of view and/or to optimize the system focus, exposure time, etc. Grating and prism based spectral imagers are in use for remote sensing applications, because an airplane (or satellite) flying over the surface of the Earth provides the system with a natural line scanning mechanism.

It should be further noted that slit-type imaging spectrometers have a major disadvantage since most of the pixels of one frame are not measured at any given time, even though the fore-optics of the instrument actually collects incident light from all of them simultaneously. The result is that either a relatively large measurement time is required to obtain the necessary information with a given signal-to-noise ratio, or the signal-to-noise ratio (sensitivity) is substantially reduced for a given measurement time. Furthermore, slit-type spectral imagers require line scanning to collect the necessary information for the whole scene, which may introduce inaccuracies to the results thus obtained.

Filter based spectral dispersion methods can be further categorized into discrete filters and tunable filters. In these types of imaging spectrometers the spectral image is built by filtering the radiation for all the pixels of the scene simultaneously at a different wavelength at a time by inserting in succession narrow band filters in the optical path, or by electronically scanning the bands using acousto-optic tunable filters (AOTF) or liquid-crystal tunable filter (LCTF), see below. Similarly to the slit type imaging spectrometers equipped with a grating or prism as described above, while using filter based spectral dispersion methods, most of the radiation is rejected at any given time. In fact, the measurement of the whole image at a specific wavelength is possible because all the photons outside the instantaneous wavelength being measured are rejected and do not reach the CCD.

Tunable filters, such as AOTFs and LCTFs have no moving parts and can be tuned to any particular wavelength in the spectral range of the device in which they are implemented. One advantage of using tunable filters as a dispersion method for spectral imaging is their random wavelength access; i.e., the ability to measure the intensity of an image at a number of wavelengths, in any desired sequence without the use of filter wheels. However, AOTFs and LCTFs have the disadvantages of (i) limited spectral range (typically, $\lambda_{max}=2\lambda_{min}$) while all other radiation that falls outside of this spectral range must be blocked, (ii) temperature sensitivity, (iii) poor transmission, (iv) polarization sensitivity, and (v) in the case of AOTFs an effect of shifting the image during wavelength scanning, demanding careful and complicated registration procedures thereafter.

All these types of filter and tunable filter based systems have not been used successfully and extensively over the years in spectral imaging for any application, because of their limitations in spectral resolution, low sensitivity, and lack of easy-to-use and sophisticated software algorithms for interpretation and display of the data.

A method and apparatus for spectral analysis of images which have advantages in the above respects was disclosed in U.S. patent application Ser. No. 08/392,019 to Cabib et al., filed Feb. 21st, 1995, now U.S. Pat. No. 5,539,517, issued Jul. 23, 1996, which is incorporated by reference as if fully set forth herein, with the objective to provide a method and apparatus for spectral analysis of images which better utilizes all the information available from the collected incident light of the image to substantially decrease the required frame time and/or to substantially increase the signal-to-noise ratio, as compared to the conventional slit- or filter type imaging spectrometer and does not involve line scanning. According to this invention, there is provided a method of analyzing an optical image of a scene to determine the spectral intensity of each pixel thereof by collecting incident light from the scene; passing the light through an interferometer which outputs modulated light corresponding to a predetermined set of linear combinations of the spectral intensity of the light emitted from each pixel; focusing the light outputted from the interferometer on a detector array, scanning the optical path difference (OPD) generated in the interferometer for all pixels independently and simultaneously and processing the outputs of the detector array (the interferograms of all pixels separately) to determine the spectral intensity of each pixel thereof. This method may be practiced by utilizing various types of interferometers wherein the OPD is varied to build the interferograms by moving (e.g., rotating, translating) the entire interferometer, an element within the interferometer, or the angle of incidence of the incoming radiation. In all of these cases, when the scanner completes one scan of the interferometer, the interferograms for all pixels of the scene are completed.

Apparatuses in accordance with the above features differ from the conventional slit- and filter type imaging spectrometers by utilizing an interferometer as described above, therefore not limiting the collected energy with an aperture or slit or limiting the incoming wavelength with narrow band interference or tunable filters, thereby substantially increasing the total throughput of the system. Thus, interferometer based apparatuses better utilize all the information available from the incident light of the scene to be analyzed, thereby substantially decreasing the measuring time and/or substantially increasing the signal-to-noise ratio (i.e., sensitivity). The sensitivity advantage that interferometric spectroscopy has over the filter and grating or prism methods is known in the art as the multiplex or Fellgett advantage [see, Chamberlain (1979) The principles of interferometric spectroscopy, John Wiley and Sons, pp. 16–18 and p. 263].

Consider, for example, the "whisk broom" design described in John B. Wellman (1987) Imaging Spectrometers for Terrestrial and Planetary Remote Sensing, SPIE Proceedings, Vol. 750, p. 140. Let n be the number of detectors in the linear array, m×m the number of pixels in a frame and T the frame time. The total time spent on each pixel in one frame summed over all the detectors of the array is $nT/m^2$. By using the same size array and the same frame rate in a method according to the invention described in U.S. Pat. No. 5,539,517, the total time spent summed over all the detectors on a particular pixel is the same, $nT/m^2$. However, whereas in the conventional grating or prism method the energy seen by every detector at any time is of the order of 1/n of the total, because the wavelength resolution is 1/n of the range, in a method according to the invention described in U.S. patent application Ser. No. 08/392,019 the energy is of the order of unity, because the modulating function is an oscillating function (e.g., sinusoidal (Michelson) or similar periodic function such as low finesse Airy function with Fabry-Perot) whose average over a large OPD range is 50%. Based on the standard treatment of the Fellgett advantage (or multiplex advantage) described in interferometry textbooks [for example, see, Chamberlain (1979) The principles of interferometric spectroscopy, John Wiley and Sons, pp. 16–18 and p. 263], it is possible to show that devices according to this invention have measurement signal-to-noise ratios which are improved by a factor of $n^{0.5}$ in the cases of noise limitations in which the noise level is independent of signal (system or background noise limited situations) and by the square root of the ratio of the signal at a particular wavelength to the average signal in the spectral range, at wavelengths of a narrow peak in the cases the limitation is due to signal photon noise. Thus, according to the invention described in U.S. Pat. No. 5,539,517, all the required OPDs are scanned simultaneously for all the pixels of the scene in order to obtain all the information required to reconstruct the spectrum, so that the spectral information is collected simultaneously with the imaging information. This invention can be used with many different optical configurations, such as a telescope for remote sensing, a microscope for laboratory analysis, fundus cameras for retinal imaging, fiber optics and endoscopes for industrial monitoring and medical imaging, diagnosis, therapy and others.

In a continuation application (U.S. patent application Ser. No. 08/571,047 to Cabib et al., filed Dec. 12, 1995, which is incorporated by reference as if fully set forth herein) the objective is to provide spectral imaging methods for biological research, medical diagnostics and therapy, which methods can be used to detect spatial organization (i.e., distribution) and to quantify cellular and tissue natural constituents, structures, organelles and administered components such as tagging probes (e.g., fluorescent probes) and drugs using light transmission, reflection, scattering and fluorescence emission strategies, with high spatial and spectral resolutions. In U.S. patent application Ser. No. 08/571, 047, the use of the spectral imaging apparatus described in U.S. Pat. No. 5,539,517 for interphase fluorescent in situ hybridization of as much as six loci specific probes (each loci located on a different chromosome) was demonstrated, as well as additional biological and medical applications.

Spectral bio-imaging systems are potentially useful in all applications in which subtle spectral differences exist between chemical constituents whose spatial distribution and organization within an image are of interest. The measurement can be carried out using virtually any optical system attached to the system described in U.S. Pat. No. 5,539,517, for example, an upright or inverted microscope, a fluorescence microscope, a macro lens, an endoscope or a fundus camera. Furthermore, any standard experimental method can be used, including light transmission (bright field and dark field), auto-fluorescence and fluorescence of administered probes, etc.

Fluorescence measurements can be made with any standard filter cube (consisting of a barrier filter, excitation filter and a dichroic mirror), or any customized filter cube for special applications, provided the emission spectra fall within the spectral range of the system sensitivity. Spectral bio-imaging can also be used in conjunction with any standard spatial filtering method such as dark field and phase contrast, and even with polarized light microscopy. The effects on spectral information when using such methods must, of course, be understood to correctly interpret the measured spectral images.

In U.S. patent application Ser. No. 08/824,234, filed Mar. 25, 1997, which is incorporated by reference as if fully set forth herein, a method of cell classification is described with the objective of obtaining morphometric data of analyzed cells based on specific spectral signatures of their organelles or constituents. According to this method spectral data is collected from every pixel of an analyzed cell and the spectra thus obtained are each compared to a library of spectra in what is known in the art as a classification procedure. Thereafter, each pixel is given a color according to the classification results. As a result, a detailed and clear morphometric image is obtained and morphometric data can be easily extracted. Since cancer cells are known to go through characterizing morphometric changes during their development, the method can be used to differentiate between cancer and normal cells, to determine the stage of cancer, etc., nearly automatically and in a highly objective manner.

For example, in the evaluation of infiltrating breast carcinomas, ductal and lobular carcinomas may present similar histological appearances [Azzopardi J G, Chepick O F, Hartmann W H, Jafarey N A, Lombart-Bosch A, Ozello L (1982). The World Health Organization histological typing of breast tumors. 2nd ed. Am J Clin Pathol 78:806–816]. Some quantitative histopathological variables have been identified by morphological methods as an aid to the differentiation between ductal and lobular carcinomas [Ladekarl M and Sorensen F B (1993). Quantitative histopathological variables in in situ and invasive ductal carcinoma of the breast. AMPIS 101(12):895–903]. The attempts to grade and to differentiate, or in other words to classify the tumors have been based mainly on nuclear morphology and chromatin structure [Ladekarl M and Sorensen F B (1993). Quantitative histopathological variables in in situ and invasive ductal carcinoma of the breast. AMPIS 101(12):895–903; Cornelisse C J, de Konig H R, Moolenaar A J (1984). Image and flow cytometric analysis of DNA content in breast cancer; relation to estrogen receptor content and lymph node involvement. Anal Quant Cytol Histol 4:9–18; Stenkvist B, Westman-Naeser S, Holmquist J (1978). Computerized nuclear morphology as an objective method for characterizing human cancer cell populations. Cancer Res 38:4688–4977; Dawson A E, Austin R E, Weinberg D S (1991). Nuclear grading of breast carcinoma by image analysis. Classification by multivariate and neural network analysis. Am J Clin Pathol 95:S29–S37]. Morphometric classification of other tumor types, such as, but not limited to leukemias, lymphomas, sarcomas and other carcinomas [see, for example, Clarke A M, Reid W A and Jack A S (1993) Combined proliferating cell nuclear antigen and morphometric analysis in the diagnosis of cancerous lymphoid infiltrates. J. Clin. Pathol. 46:129–134] are also vastly implemented both in research and in medical practice.

Nevertheless, as was recently published following an NIH workshop which evaluated the reliability of histopathological diagnosis by the best pathologists in the field of cancer diagnostics, there is a discordance among expert pathologists in the diagnosis of neoplasm. Based on this workshop, it was concluded that histopathological decision making is 100% subjective, regardless of the origin of specimen and that this state of affairs in histopathological diagnosis is not confined to a specific tumor, but is applicable to differential diagnosis in every organ. These conclusions were published in an editorial by A Bernard Ackerman (1996) entitled "Discordance among expert pathologists in diagnosis of melanocytic neoplasm", in Human pathology 27:1115–1116.

Although, spectrally resolved and therefore objective morphometric analysis provides an excellent tool for cancer cell detection, other objective procedures may prove more suitable in some cases, either alone or in combination with morphometric analysis or other cancer cell detection methods.

There is thus a widely recognized need for, and it would be highly advantageous to have a spectral method for determining a ratio between dyes used to stain cells, which can be used for objective cancer cell detection.

SUMMARY OF THE INVENTION

According to the present invention there is provided a method for cancer cell detection.

According to further features in preferred embodiments of the invention described below, the method comprising the steps of (a) staining an analyzed sample with at least first and second dyes, the dyes being selected such that the first dye better adheres to normal cells whereas the second dye better adheres to cancer cells; (b) spectrally imaging the sample through an optical device being optically connected to an imaging spectrometer thereby obtaining a spectrum of each pixel of the sample; (c) based on the spectra, evaluating concentrations of the first and second dyes for each of the pixels; and (d) based on the concentrations detecting the presence of cancer cells in the sample.

According to still further features in the described preferred embodiments the method further comprising the step of (e) presenting at least one image indicating the concentrations.

According to still further features in the described preferred embodiments the image includes first and second decomposition coefficients maps.

According to still further features in the described preferred embodiments the image includes a concentration ratios map.

According to still further features in the described preferred embodiments the first and second dyes are selected from the pairs of dyes consisting of Hematoxylin and Eosin and thiazin and Eosin.

According to still further features in the described preferred embodiments the obtainment of the spectrum of each pixel of step (b) is effected by (i) collecting incident light simultaneously from all pixels of the sample using collimating optics; (ii) passing the incident collimated light through an interferometer system having a number of elements, so that the light is first split into two coherent beams which travel in different directions inside the interferometer and then the two coherent beams recombine to interfere with each other to form an exiting light beam; (iii) passing the exiting light beam through a focusing optical system which focuses the exiting light beam on a detector having a two-dimensional array of detector elements, so that at each instant each of the detector elements is the image of one and always the same pixel of the sample for the entire duration of the measurement, so that the real image of the sample is stationary on the plane of the detector array and at any time during the measurement the image is still visible and recognizable, and so that each of the detector elements produces a signal which is a particular linear combination of light intensity emitted by the pixel at different wavelengths, wherein the linear combination is a function of the instantaneous optical path difference; (iv) scanning one or more of the elements of the interferometer system, so that the optical path difference between the two coherent beams generated by the interferometer system is scanned simultaneously for all the pixels of the sample; and (v) recording signals of each of the detector elements as function of time using a recording device to form a spectral cube of data.

According to still further features in the described preferred embodiments the optical device is a microscope.

According to still further features in the described preferred embodiments the imaging spectrometer includes an element selected from the group consisting of a dispersion element, a filter and an interferometer.

According to still further features in the described preferred embodiments the evaluation of the concentrations is a relative evaluation.

According to still further features in the described preferred embodiments the sample is of a prostate.

According to still further features in the described preferred embodiments evaluating concentrations of the first and second dyes for each of the pixels is effected by (i) converting the spectra of the pixels into an absorption spectral image; (ii) obtaining a reference absorption spectrum for each of the first and second dyes; (iii) using the reference absorption spectra for decomposing the absorption spectral image and finding optimal first and second decomposition coefficients; and (iv) using the first and second decomposition coefficients for evaluating the concentrations.

According to still further features in the described preferred embodiments converting the spectra of the pixels into an absorption spectral image is effected in accordance with the Lambert Beer law using a background reference spectrum.

According to still further features in the described preferred embodiments each of the reference absorption spectra is determined by measuring a reference spectrum for each of the dyes and using a background reference spectrum in accordance with the Lambert Beer law for calculating each of the reference absorption spectra.

According to still further features in the described preferred embodiments finding the optimal first and second decomposition coefficients is effected by a minimal square error algorithm.

According to still further features in the described preferred embodiments using the first and second decomposition coefficients for evaluating the concentrations is effected by providing first and second monochromatic coefficients maps for each of the first and second dyes.

According to still further features in the described preferred embodiments the method further comprising the step of, according to the coefficients maps, determining a ratio between the concentrations of the dyes for each of the pixels.

According to still further features in the described preferred embodiments the method further comprising the step of providing a concentration ratios map.

According to still further features in the described preferred embodiments the concentration ratios map is effected by an algorithm selected from the group consisting of an RGB algorithm and a classification algorithm.

According to still further features in the described preferred embodiments the concentration ratios map is provided by joining the first and second monochromatic maps, each of the monochromatic maps is of a different monochrome, for obtaining a composite image.

According to still further features in the described preferred embodiments the method further comprising the step of providing a scatter plot of the ratios.

The present invention successfully addresses the shortcomings of the presently known configurations by providing a method of detection of cancer cells. The method according to the invention is fully objective and can be easily automated. Additional advantages and objectives of the present invention are described in the following sections.

BRIEF DESCRIPTION OF THE DRAWINGS

The invention herein described, by way of example only, with reference to the accompanying drawings, wherein.

DESCRIPTION OF THE PREFERRED EMBODIMENTS

The present invention is of a spectral bio-imaging method which can be used for cancer cell detection. Specifically, the method of the present invention provides, for each pixel of an examined cell sample, a ratio between at least two dyes which were used to stain the cell and presents the results in a meaningful way. Apparently, cancer and non-cancer cells posses different ratios and therefore the method is applicable for cancer cell detection.

For purposes of better understanding the present invention, as illustrated in FIGS. 4–10 of the drawings, reference is first made to the construction and operation of some spectral imaging systems (i.e., imaging spectrometers).

SPECTRAL IMAGING

Figure 1:
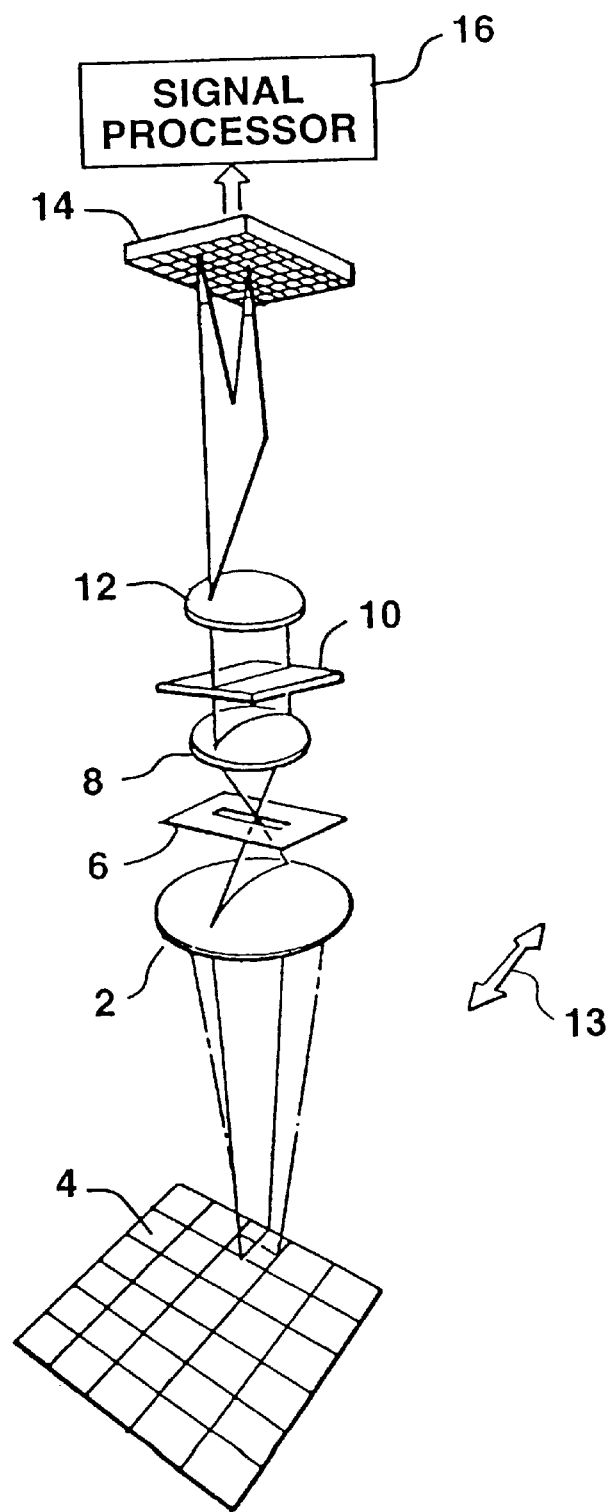
FIG. 1 illustrates a conventional (prior art) slit-type imaging spectrometer.

A conventional (i.e., prior art) slit-type imaging spectrometer utilizing a two-dimensional array of detectors as illustrated in FIG. 1.

Thus, the prior art slit-type imaging spectrometer as illustrated in FIG. 1 comprises a collection optical system as indicated at 2, for collecting the incident light from a scene, schematically indicated at 4 and focusing the substantially parallel light of the scene 4 onto a first focal plane occupied by a slit 6 to define the field of view. The light exiting from slit 6 is collimated in a collimator lens 8 and is passed through a spectral dispersion element 10 (e.g., a grating or a prism) to separate the various wavelengths. The output from spectral dispersion element 10 is focused by a focusing lens 12 onto a two-dimensional detector array 14 in a second focal plane. The output of detector array 14 is fed to a signal processor 16.

In the two-dimensional array of detectors 14 illustrated in the prior art imaging spectrometer of FIG. 1, the movement of the system (e.g., a raster movement or line scanning indicated by arrow 13) effects the scanning along one dimension. The scanning along the second dimension is effected by the slit 6 which is oriented perpendicularly to the direction of movement of the system. The slit 6 thus assures that each detector within the array 14 sees only the contribution of one pixel at a single wavelength at any time. This is necessary to separate the spectra of each pixel.

As mentioned in the background section and hereinabove, the disadvantage of the prior art method illustrated in FIG. 1 is that most of the pixels of one frame are not measured at any given time even though the optical system 2 actually collects light energy from all of them simultaneously. As a result, the required frame time is significantly increased, and/or the signal-to-noise ratio (sensitivity) is substantially decreased with respect to a system which does not have the need for such a slit.

Figure 2:
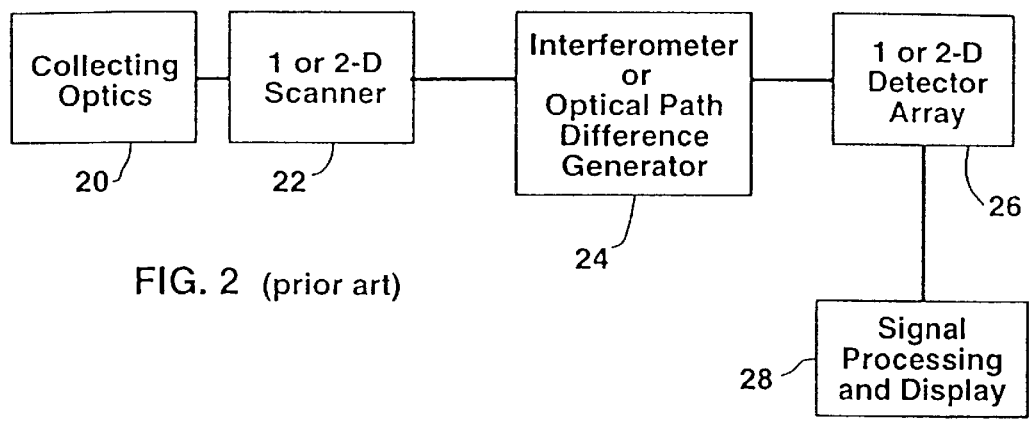
FIG. 2 is a block diagram illustrating the main components of an imaging spectrometer constructed in accordance with U.S. Pat. No. 5,539,517 (prior art)

FIG. 2 is a block diagram illustrating the main components of an improved prior art imaging spectrometer disclosed in U.S. patent application Ser. No. 08/392,019 to Cabib et al., filed Feb. 21st, 1995, now U.S. Pat. No. 5,539,517, issued Jul. 23, 1996, which is incorporated by reference as if fully set forth herein. This imaging spectrometer is constructed highly suitable to implement the methods of the present invention.

Thus, the prior art imaging spectrometer of FIG. 2 includes: a collection optical system, generally designated 20; a one-dimensional scanner, as indicated by block 22; an optical path difference (OPD) generator or interferometer, as indicated by block 24; a one-dimensional or two-dimensional detector array, as indicated by block 26; and a signal processor and display, as indicated by block 28.

A critical element in system 20 is the OPD generator or interferometer 24, which outputs modulated light corresponding to a predetermined set of linear combinations of the spectral intensity of the light emitted from each pixel of the scene to be analyzed. The output of the interferometer is focused onto the detector array 26. Thus, all the required optical phase differences are scanned simultaneously for all the pixels of the field of view, in order to obtain all the information required to reconstruct the spectrum of each pixel. The spectra of all the pixels in the scene are thus collected simultaneously with the imaging information, thereby permitting analysis of the image in a real-time manner.

The apparatus according to U.S. Pat. No. 5,539,517 may be practiced in a large variety of configurations. Specifically, the interferometer used may be combined with other mirrors as described in the relevant Figures of U.S. Pat. No. 5,539,517.

Thus, according to U.S. Pat. No. 5,539,517, few alternative types of interferometers may be employed. These include (i) a moving type interferometer in which the OPD is varied to modulate the light, namely, a Fabry-Perot interferometer with scanned thickness; (ii) a Michelson type interferometer which includes a beamsplitter receiving the beam from an optical collection system and a scanner, and splitting the beam into two paths; (iii) a Sagnac interferometer optionally combined with other optical means in which interferometer the OPD varies with the angle of incidence of the incoming radiation, and (iv) a four-mirror plus beamsplitter interferometer as further described and exemplified in the cited U.S. Patent application.

Figure 3:
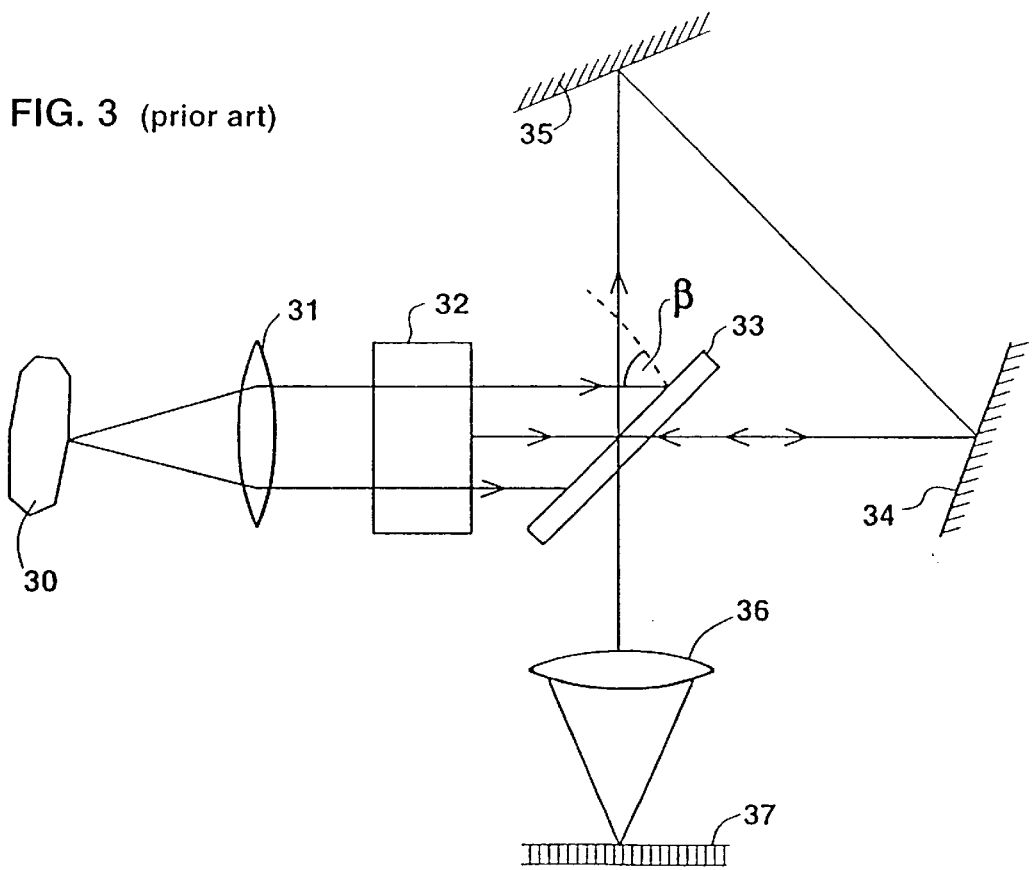
FIG. 3 illustrates a non-moving type interferometer, namely, a Sagnac interferometer, as used in an imaging spectrometer in accordance with U.S. Pat. No. 5,539,517 (prior art)

FIG. 3 illustrates an imaging spectrometer constructed in accordance with U.S. Pat. No. 5,539,517 utilizing an interferometer in which the OPD varies with the angle of incidence of the incoming radiation. A beam entering the interferometer at a small angle to the optical axis undergoes an OPD which varies linearly with this angle.

In the interferometer of FIG. 3, all the radiation from source 30 in all the pixels, after being collimated by an optical collection system 31, is scanned by a mechanical scanner 32. The light is then passed through a beamsplitter 33 to a first reflector 34 and then to a second reflector 35, which reflects the light back through the beamsplitter 33 and then through a focusing lens 36 to an array of detectors 37 (e.g., a CCD). This beam interferes with the beam which is reflected by 33, then by second reflector 35, and finally by first reflector 34.

To perform the OPD scan the whole interferometer is rotated, or it is optionally combined with other optical elements which are rotated; alternatively, in the case of Michelson or Fabry Perot the scan is performed by the translation of a mirror.

At the end of a single scan, every pixel has been measured through all the OPD's, and therefore the spectrum of each pixel of the scene can be reconstructed by Fourier transformation. A beam parallel to the optical axis is compensated, and a beam at an angle (θ) to the optical axis undergoes an OPD which is a function of the thickness of the beamsplitter 33, its index of refraction, and the angle θ. The OPD is proportional to θ for small angles. By applying the appropriate inversion, and by careful bookkeeping, the spectrum of every pixel is calculated.

In the configuration of FIG. 3 the ray which is incident on the beamsplitter at an angle β(β=45° in FIG. 3) goes through the interferometer with an OPD=0, whereas a ray which is incident at a general angle β−θ undergoes an OPD given by Equation 1:

$$OPD(\beta, \theta, t, n) = t[(n^2 - \sin^2(\beta + \theta))^{0.5} - (n^2 - \sin^2(\beta - \theta))^{0.5} + 2 \sin \beta \sin \theta] \quad (1)$$

where θ is the angular distance of a ray from the optical axis or interferometer rotation angle with respect to the central position; t is the thickness of the beamsplitter; and n is the index of refraction of the beamsplitter.

It follows from Equation 1 that by scanning both positive and negative angles with respect to the central position, one can get a double-sided interferogram for every pixel, which helps eliminate phase errors giving more accurate results in the Fourier transform calculation. The scanning amplitude determines the maximum OPD reached, which is related to the spectral resolution of the measurement. The size of the angular steps determines the OPD step which is, in turn, dictated by the shortest wavelength to which the system is sensitive. In fact, according to the sampling theorem [see, Chamberlain (1979) The principles of interferometric spectroscopy, John Wiley and Sons, pp. 53–55], this OPD step must be smaller than half the shortest wavelength to which the system is sensitive.

Another parameter which should be taken into account is the finite size of a detector element in the matrix. Through the focusing optics, the element subtends a finite OPD in the interferometer which has the effect of convolving the interferogram with a rectangular function. This brings about, as a consequence, a reduction of system sensitivity at short wavelengths, which drops to zero for wavelengths equal to or below the OPD subtended by the element. For this reason, one must ensure that the modulation transfer function (MTF) condition is satisfied, i.e., that the OPD subtended by a detector element in the interferometer must be smaller than the shortest wavelength at which the instrument is sensitive.

Thus, imaging spectrometers constructed in accordance with the invention disclosed in U.S. Pat. No. 5,539,517 do not merely measure the intensity of light coming from every pixel in the field of view, but also measure the spectrum of each pixel in a predefined wavelength range. They also better utilize all the radiation emitted by each pixel in the field of view at any given time, and therefore permit, as explained above, a significant decrease in the frame time and/or a significant increase in the sensitivity of the spectrometer. Such imaging spectrometers may include various types of interferometers and optical collection and focusing systems, and may therefore be used in a wide variety of applications, including medical diagnostic and therapy and biological research applications, as well as remote sensing for geological and agricultural investigations, and the like.

An imaging spectrometer in accordance with the invention disclosed in U.S. Pat. No. 5,539,517 was developed by Applied Spectral Imaging (ASI) Ltd., Industrial Park, Migdal Haemek, Israel and is referred hereinbelow as SPECTRACUBE™. The SPECTRACUBE™ system optically connected to a variety of optical devices was used to implement the methods of the present invention. The SPECTRACUBE™ system has the following characteristics, listed hereinbelow in Table 1:

TABLE 1

| Parameter | Performance |
| --- | --- |
| Spatial resolution: | 30/M $\mu m$ (M = effective microscope or fore optics magnification) |
| Field of View: | 8/M millimeter |
| Sensitivity: | 20 milliLux (for 100 msec integration time, increases for longer integration times linearly with $\sqrt{T}$) |
| Spectral range: | 400–1000 nm |
| Spectral resolution: | 4 nm at 400 nm (16 nm at 800 nm) |
| Acquisition time: | 5–50 sec, typical 15–25 sec |
| FFT processing time: | 20–180 sec, typical 60 sec |

The SPECTRACUBE™ system easily attaches to any microscope or macro lens with, for example, C-mount or F-mount connectors, and can stand in any orientation during the measurement. The system may as well be connected to other magnification means and to various types of endoscopes and cameras. Therefore, spectral images of cells and tissues in various magnification and lighting strategies may be obtained.

The SPECTRACUBE™ system has numerous utilities. For examples of the use of the SPECTRACUBE™ system for various biological applications, the reader is referred to U.S. Patent application Ser. No. 08/571,047, and to E. Schroeck et al. (1996) Multicolor spectral karyotyping of human chromosomes. Science, 273, 494–497; Garini et al. (1996) Spectral Karyotyping, Bioimaging 4, 65–72; Malik et al. (1996) Fourier transform multipixel spectroscopy and spectral imaging of protoporphyrin in single melanoma cells, Photochemistry and photobiology 63, 608–614; Malik et al. (1996) Fourier transform multipixel spectroscopy for quantitative cytology, Journal of Microscopy 182, 133–140; Garini et al. (1996) Spectral Bio-Imaging, Fluorescence imaging spectroscopy and microscopy, chapter 4, ed. X. F. Wang and B. Herman, Chemical Analysis Series, Vol. 137, John Wiley and Sons; Soenksen et al. (1996) Use of novel spectral bio-imaging system as an imaging oximeter in intact rat brain, SPIE Proceedings 2679; Liyanage et al. (1996) Multicolor spectral karyotyping of mouse chromosomes, Nature Genetics 14, 312–315; all are incorporated by reference as if fully set forth herein.

The prior art SPECTRACUBE™ system is used herein to acquire spectral data of every pixel of cancer cells. However, any spectral imager, i.e., an instrument that measures and stores in memory for later retrieval and analysis the spectrum of light emitted by every point of an object which is placed in its field of view, including filter (e.g., acousto-optic tunable filters (AOTF) or liquid-crystal tunable filter (LCTF)) and dispersive element (e.g., grating or prism) based spectral imagers can be used to acquire the required spectral data. Therefore, it is intended not to limit the scope of the present invention for use of any specific type of spectral imager.

DISPLAY AND ANALYSIS OF SPECTRAL IMAGES a. General

As mentioned above, a spectral image is a three dimensional array of data, $I(x,y,\lambda)$, that combines spectral information with spatial organization of the image. As such, a spectral image is a set of data called a spectral cube, due to its dimensionality, which enables the extraction of features and the evaluation of quantities that are difficult, and in some cases even impossible, to obtain otherwise. Since both spectroscopy and digital image analysis are well known fields that are covered by an enormous amount of literature [see, for example, Jain (1989) Fundamentals of Digital Image Processing, Prentice-Hall International], the following discussion will focus primarily on the benefit of combining spectroscopic and imaging information in a single data set, i.e., a spectral cube.

One possible type of analysis of a spectral cube is to use spectral and spatial data separately, i.e., to apply spectral algorithms to the spectral data and two-dimensional image processing algorithms to the spatial data.

As an example for a spectral algorithm consider an algorithm computing the similarity between a reference spectrum and the spectra of all pixels (i.e., similarity mapping) resulting in a gray (or other color) scale image (i.e., a similarity map) in which the intensity at each pixel is proportional to the degree of 'similarity'. This gray scale image can then be further analyzed using image processing and computer vision techniques (e.g., image enhancement, pattern recognition, etc.) to extract the desired features and parameters. In other words, similarity mapping involves computing the integral of the absolute value of the difference between the spectrum of each pixel of the spectral image with respect to a reference spectrum (either previously memorized in a library, or belonging to a pixel of the same or other spectral image), and displaying a gray level or pseudocolor (black and white or color) image, in which the bright pixels correspond to a small spectral difference, and dark pixels correspond to a large spectral difference, or vice versa.

Similarly, classification mapping perform the same calculation as described for similarity mapping, yet takes several spectra as reference spectra, and paints each pixel of the displayed image with a different predetermined pseudocolor, according to its classification as being most similar to one of the several reference spectra. Both, similarity and classification mapping may employ any of the four following Equations (2–5).

The reference spectrum can be one corresponding to a pixel in the same image, or from a library or from another image.

There are many similarity map functions known in the literature, four are given hereinbelow (Equations 2–5):

$$G_{x,y}^{(1)} = \frac{I_{max}^2}{40\left(\left(\frac{1}{n}\sum_\lambda (I_{xy}(\lambda) - R_\lambda)^2\right)^{\frac{1}{2}} + \frac{I_{max}}{40}\right)} \quad (2)$$

$$G_{x,y}^{(2)} = \frac{I_{max}^2}{20\left(\left(\frac{1}{n}\sum_\lambda (I_{xy}(\lambda) - R_\lambda)^2\right)^{\frac{1}{2}} + \frac{I_{max}}{20}\right)} \quad (3)$$

$$G_{x,y}^{(3)} = \frac{I_{max}^2}{40\left(\frac{R_{max}}{S_{max}}\left(\frac{1}{n}(I_{xy}(\lambda) - R_\lambda)^2\right)^{\frac{1}{2}} + \frac{I_{max}}{40}\right)} \quad (4)$$

$$G_{x,y}^{(4)} = \frac{I_{max}^2}{40\left(\frac{R_{max}}{T_{max}}\left(\frac{1}{n}(\langle I_{x,y}(l)\rangle - R_l)^2\right)^{\frac{1}{2}} + \frac{I_{max}}{40}\right)} \quad (5)$$

where $I_{max}$ is the maximum intensity of the image, $G_{x,y}$ is the brightness with 20 which a pixel (of coordinates x and y) is displayed on the screen, $I_{x,y}(\lambda)$ is its spectrum, $\langle I_{xy}(\lambda)\rangle$ is the average of $I_{xy}(\lambda)$ over the group of 3×3 neighboring pixels, $S_{max}$ is the peak intensity of $I_{xy}(\lambda)$, $T_{max}$ is the peak intensity of $\langle I_{xy}(\lambda)\rangle$, $R_{80}$ is the reference spectrum with respect to which the similarity map is calculated, $R_{max}$ is the peak intensity of the reference spectrum $R_\lambda$ and n is the number of wavelengths of the measurement.

When similarity mapping is performed, it is clear that according to the above Equations 2–5, in all cases, the more a pixel spectrum is similar to the reference spectrum, the brighter it will be displayed on the screen.

On the other hand, when classification is performed, a calculation using the spectrum of each of the pixels of the image, one at a time, and of each of the few reference spectra, one at a time, is performed (preferably after normalization of all spectra to a 0–100% intensity range), and the analyzed pixel is given a preselected arbitrary color according to the reference spectra to which it is most similar using for example a minimal square error calculation, as well known in the art.

It is also possible to apply spectral image algorithms based on non-separable operations; i.e., algorithms that include both local spectral information and spatial correlation between adjacent pixels (one of these algorithms is, as will be seen below, a principal component analysis).

One of the basic needs that arise naturally when dealing with any three-dimensional (3D) data structure such as a spectral cube (i.e., $I(x,y,\lambda)$), is visualizing that data structure in a meaningful way. Unlike other types of 3D data such as topographic data, $D(x,y,z)$, obtained for example by a confocal microscope, where each point represents, in general, the intensity at a different locations (x,y,z) in three-dimensional space, a spectral image is a sequence of images representing the intensity of the same two-dimensional plane (i.e., the sample) at different wavelengths. For this reason, the two most intuitive ways to view a spectral cube of data is to either view the image plane (spatial data) or the intensity of one pixel or a set of pixels as function of wavelength in a three-dimensional mountain-valley display. In general, the image plane can be used for displaying either the intensity measured at any single wavelength or the gray scale image that results after applying a spectral analysis algorithm, over a desired spectral region, at every image pixel. The spectral axis can, in general, be used to present the resultant spectrum of some spatial operation performed in the vicinity of any desired pixel (e.g., averaging the spectrum).

It is possible, for example, to display the spectral image as a gray scale image, similar to the image that might be obtained from a simple monochrome camera, or as a multicolor image utilizing one or several artificial colors to highlight and map important features. Since such a camera simply integrates the optical signal over the spectral range (e.g., 400 nm to 760 nm) of the CCD array, the 'equivalent' monochrome CCD camera image can be computed from the 3D spectral image data base by integrating along the spectral axis, as follows:

$$gray\_scale(x, y) = \int_{\lambda_2}^{\lambda_1} w(\lambda) \cdot I(x, y, \lambda) d\lambda \quad (6)$$

In Equation 6, $w(\lambda)$ is a general weighting response function that provides maximum flexibility in computing a variety of gray scale images, all based on the integration of an appropriately weighted spectral image over some spectral range. For example, by evaluating Equation 6 with three different weighting functions, $\{w_r(\lambda), w_g(\lambda), w_b(\lambda)\}$, corresponding to the tristimulus response functions for red (R), green (G) and blue (B), respectively, it is possible to display a conventional RGB color image. It is also possible to display meaningful non-conventional (pseudo) color images.

Figure 4:
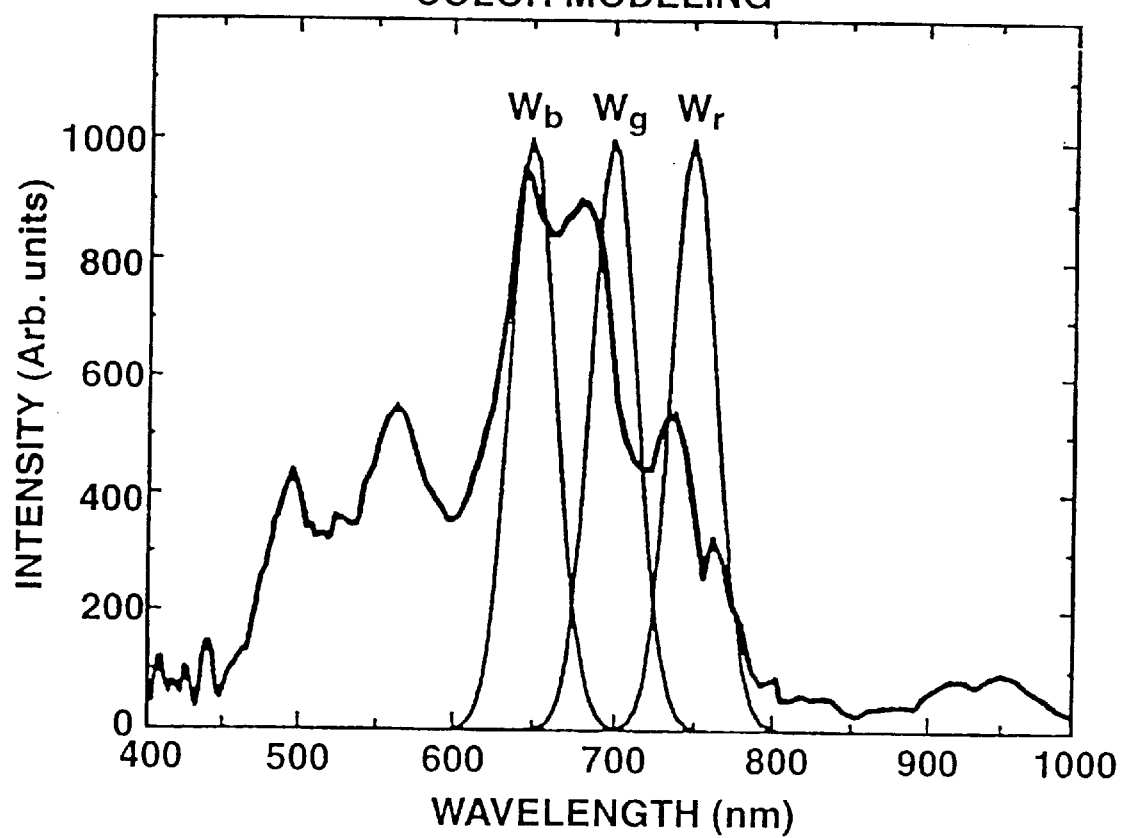
FIG. 4 shows a definition of pseudo-RGB (Red, Green and Blue) colors for emphasizing chosen spectral ranges. The intensity for each pseudo-color is calculated by integrating the area under the curve, after multiplying it by one of the curves.

FIG. 4 presents an example of the power of this simple algorithm. Consider choosing $\{w_r, w_g, w_b\}$ to be Gaussian functions distributed "inside" a spectrum of interest, the resulting pseudo-color image that is displayed in this case emphasizes only data in the spectral regions corresponding to the weighting functions, enabling spectral differences in these three regions to be detected more clearly.

b. Point Operations

Point operations are defined as those that are performed on single pixels, (i.e., do not involve more than one pixel at a time). For example, in a gray scale image, a point operation can be one that maps the intensity of each pixel (intensity function) into another intensity according to a predetermined transformation function. A particular case of this type of transformation is the multiplication of the intensity of each pixel by a constant.

The concept of point operations can also be extended to spectral images: here each pixel has its own intensity function (spectrum), i.e., an n-dimensional vector $V_1(\lambda)$; $\lambda \in [\lambda_1, \lambda_n]$. A point operation applied to a spectral image can be defined as one that maps the spectrum of each pixel into a scalar (i.e., an intensity value) according to a transformation function:

$$v_2 = g(V_1(\lambda)); \lambda \in [\lambda_1, \lambda_n] \quad (7)$$

Building a gray scale image according to Equation 7 is an example of this type of point operation. In the more general case, a point operation maps the spectrum (vector) of each pixel into another vector according to a transformation function:

$$V_2(l) = g(V_1(\lambda)); l \in [1, N], \lambda \in [\lambda_1, \lambda_n] \quad (8),$$

where $N \leq n$.

In this case a spectral image is transformed into another spectral image.

One can now extend the definition of point operations to include operations between corresponding pixels of different spectral images. An important example of this type of algorithm is optical density analysis. Optical density is employed to highlight and graphically represent regions of an object being studied spectroscopically with higher dynamic range than the transmission spectrum. The optical density is related to transmission by a logarithmic operation and is therefore always a positive function. The relation between the optical density and the measured spectra is given by Lambert Beer law:

$$OD(\lambda) = -\log_{10}\frac{I(\lambda)}{I_0(\lambda)} = -\log_{10}\tau(\lambda) \quad (9)$$

where $OD(\lambda)$ is the optical density as a function of wavelength, $I(\lambda)$ is the measured spectrum, $I_O(\lambda)$ is a measured reference spectrum, and $\tau(\lambda)$ is the spectral transmitance of the sample. Equation 9 is calculated for every pixel for every wavelength where $I_O(\lambda)$ is selected from (i) a pixel in the same spectral cube for which OD is calculated; (ii) a corresponding pixel in a second cube; and (iii) a spectrum from a library.

Note that the optical density does not depend on either the spectral response of the measuring system or the non-uniformity of the CCD detector. This algorithm is useful to map the relative concentration, and in some cases the absolute concentration of absorbers in a sample, when their absorption coefficients and the sample thickness are known.

Additional examples include various linear combination analyses, such as for example: (i) applying a given spectrum to the spectrum of each of the pixels in a spectral image by an arithmetical function such as addition, subtraction, multiplication division and combinations thereof to yield a new spectral cube, in which the resulting spectrum of each pixel is the sum, difference, product ratio or combination between each spectrum of the first cube and the selected spectrum; and (ii) applying a given scalar to the spectra of each of the pixels of the spectral image by an arithmetical function as described above.

Such linear combinations may be used, for example, for background subtraction in which a spectrum of a pixel located in the background region is subtracted from the spectrum of each of the pixels; and for a calibration procedure in which a spectrum measured prior to sample analysis is used to divide the spectrum of each of the pixels in the spectral image.

Another example includes a ratio image computation and display as a gray level image. This algorithm computes the ratio between the intensities at two different wavelengths for every pixel of the spectral image and paints each of the pixels in a lighter or darker artificial color accordingly. For example, it paints the pixel bright for high ratio, and dark for low ratio (or the opposite), to display distributions of spectrally sensitive materials.

C. Spatial-Spectral Combined Operations

In all of the spectral image analysis methods mentioned above, algorithms are applied to the spectral data. The importance of displaying the spectrally processed data as an image is mostly qualitative, providing the user with a useful image. It is also possible, however, depending on the application, to use the available imaging data in even more meaningful ways by applying algorithms that utilize the spatial-spectral correlation that is inherent in a spectral image. Spatial-spectral operations represent the most powerful types of spectral image analysis algorithms. As an example, consider the following situation:

A sample contains k cell types stained with k different fluorophores (the term 'cell' here is used both for a biological cell, and also as 'a region in the field of view of the instrument'). Each fluorophore has a distinct fluorescence emission spectrum and binds to only one of the k cell types. It is important to find the average fluorescence intensity per cell for each one of the k cell types. To achieve this task the following procedure can be used: (i) classify each pixel in the image as belonging to one of k+1 classes (k cell types plus a background) according to its spectrum; (ii) segment the image into the various cell types and count the number of cells from each type; and (iii) sum the fluorescence energy contributed by each class, and divide it by the total number of cells from the corresponding class.

This procedure makes use of both spectral and spatial data. The relevant spectral data takes the form of characteristic cell spectra (i.e., spectral "signatures"), while the spatial data consists of data about various types of cells (i.e., cell blobs) many of which appear similar to the eye. The ideal type of measurement for this type of situation is a spectral image. In the above situation, cells can be differentiated by their characteristic spectral signature. Hence, a suitable point operation will be performed to generate a synthetic image in which each pixel is assigned one of k+1 values. Assuming that the fluorescence emission spectra of the different cell types are known to be $s_i(\lambda)$; $i=1, 2, \ldots, k, \lambda \in [\lambda_1, \lambda_n]$, and the measured spectrum at each pixel (x, y) is $s_{x,y}(\lambda)$, $\lambda \in [\lambda_1, \lambda_n]$, then the following algorithm is a possible method of classification (step 1 above):

Let $e^2_i$ be the deviation of the measured spectrum from the known spectrum of the fluorophore attached to cell type i. Then, adopting a least-squares "distance" definition, one can write:

$$e_i^2 = \sum_{\lambda \in R_\lambda} (s(\lambda) - s_i(\lambda))^2 \quad (10)$$

where $R_\lambda$ is the spectral region of interest. Each point [pixel (x, y)] in the image can then be classified into one of the k+1 classes using the following criterion:

point(x,y) ∈ class $k+1$ if $e^2_i$>threshold for all $i \in [1,k]$, whereas point(x,y) ∈ class ρ if $e^2_i$<threshold, and ρ is such that $min[e^2_i]= e^2_\rho$ (11)

Steps ii and iii above (image segmentation and calculation of average fluorescence intensity) are now straightforward using standard computer vision operations on the synthetic image created in accordance with the algorithm described in Equations 10 and 11.

Another approach is to express the measured spectrum $s_{x,y}(\lambda)$ at each pixel as a linear combination of the k known fluorescence spectra $s_i(\lambda)$; $i=1, 2, \ldots, k$. In this case one would find the coefficient vector $C=[c_1, c_2, \ldots, c_k]$ that solves:

$$F = \min \sum_{\lambda \in R_\lambda} (s(\lambda) - \hat{s}(\lambda))^2 \qquad (12)$$

$$\text{where } \hat{s}(\lambda) = \sum_{i=1}^{k} c_i \cdot s_i(\lambda),$$

Solving for $$\frac{dF}{dc_i} = 0;$$

for $i=1,2,\ldots,k$ (i.e., find values of $c_i$ which minimize F) yields the matrix Equation $$C = A^{-1}B \qquad (13),$$

where A is a square matrix of dimension k with elements $$a_{m,n} = \left[\sum_{\lambda \in R_\lambda} s_m(\lambda) \cdot s_n(\lambda)\right], \qquad (14)$$

and B is a vector defined as $$b_m = \left[\sum_{\lambda \in R_\lambda} s_m(\lambda) \cdot s(\lambda)\right], \quad m, n = 1, 2, \cdots, k. \qquad (15)$$

Arithmetic operations may similarly be applied to two or more spectral cubes and/or spectra of given pixels or from a library. For example consider applying an arithmetic operations between corresponding wavelengths of corresponding pairs of pixels belonging to a first spectral cube of data and a second spectral cube of data to obtain a resulting third spectral cube of data for the purpose of, for example, averaging two spectral cubes of data, time changes follow-up, spectral normalization, etc.

In many cases, objects (e.g., cancer cells) present in a spectral image differ from one another in chemical constituents and/or structure to some degree. Using a decorrelation statistical analysis such as principal component analysis by producing covariance or correlation matrices enhances these small differences.

Decorrelation statistical analysis is directed at extracting decorrelated data out of a greater amount of data, and average over the correlated portions thereof. There are a number of related statistical decorrelation methods. Examples include but not limited to principal component analysis (PCA), canonical variable analysis and singular value decomposition, etc., of these methods PCA is perhaps the more common one, and is used according to the present invention for decorrelation of spectral data. However, considering the fact that all decorrelation statistical methods including those listed above are related to one another, there is no intention to limit the scope of the invention to use of any specific decorrelation method. Specifically, there is no intention to limit the scope of the present invention to use of principal component analysis, as any other decorrelation statistical method may be alternatively employed. Information concerning the use and operation of the above listed decorrelation statistical methods is found in R. A. Johnson and D. W. Wichen, "Applied Multivariance Statistical Analysis", third edition, Prentice Hall (1992) and T. W. Anderson, An Introduction to Multivariance Statistical Analysis, second edition, Wiley and Sons (1984), both are incorporated by reference as if fully set forth herein.

Furthermore, as will become apparent from the descriptions to follow, the implementation of a decorrelation statistical method may be done using various modifications. As the concept of the present invention is not dependent upon any specific modification, it is the intention that the scope of the present invention will not be limited to any specific modification as described below.

Principal component analysis (PCA) is one of a number of powerful techniques used in multivariate statistical analysis. It is advantageous in cases where a large number of "results", which depend on a large number of possibly correlated variables forms the basic data set. Its strength lies in the fact that this data decomposition provides a transformation to decorrelated variables, while simultaneously averaging over correlated variables.

In this paragraph the PCA technique as applied to multi-spectral images of the same object is delineated. The basic data set, i.e., the spectral cube, is composed of k spectral slices of the same object, where each spectral slice is obtained at a different spectral band. Thus, the data set is composed of the spectra of all the pixels of the object. One of the objectives of looking at such a data set can be the characterization of the pixels into groups of similar spectra. Regard each spectral slice as a vector whose elements are the image pixels arranged into the column vector using a predetermined code. Call the spectral slices $X_m$, so that the term $x_{nm}$ signifies the n-th pixel of the m-th spectral slice. In such way, the matrix $x=\{x_{nm}\}$ carries the full information, so that each column is a spectral slice. Define a matrix y derived from matrix x by subtracting from each column, the column average. The various columns of the y matrix may be correlated, so that, some of the information carried by the data is correlated. The PCA technique decorrelates the information and reduces it only to decorrelated variables, so that the amount of "real" data pixels is smaller and easier to handle.

The correlations are obtained directly by computing the covariance matrix c defined by Equation 16:

$$c = y'y \qquad (16)$$

where y' is the transpose of y. The i,j term of c is the covariance of the i-th slice with the j-th slice, i.e. if they are decorrelated this term vanishes. The diagonal of c is composed of the variances of each spectral slice, which can be regarded as a scale for the amount of information in this particular slice. Alternatively, this variance (its square root) can be regarded as the average contrast of this particular slice.

Linear algebra describes this situation as follows. The objects of interest (the pixels of the spectral slices, k of them) are points in a k dimensional space. The fact that the covariance matrix c shows correlations is represented by its having a rank smaller than k. This situation is called degeneracy and it means that the k (narrow band) spectral slices provide too much data relative to the information content. Reduction of the data is performed by finding the eigen system of the covariance matrix. Formally, this operation means that one has to find k vectors $v_m$ called eigenvectors and k scalars $\lambda_m$ called eigenvalues so that (Equation 17):

$$c \cdot v_m = \lambda_m v_m \text{ for } m=1,2,\ldots,k \qquad (17)$$

In a case where the data is correlated, some of the eigenvalues vanish. The number of non-vanishing eigenvalues defines the dimension of the information, which dimension is smaller than k. The corresponding eigenvectors define a subspace in the original k space in which the full information content is represented. Furthermore, the information in each new dimension is completely decorrelated to the information in the other dimensions. Thus in the new space the full information content is represented in a decorrelated manner so that it can be easily used for classification purposes. For further details regarding the principal component analysis, the reader is referred to Martens and Naes (1989) Multivariate Calibration, John Wiley & Sons, Great Britain; and to Esbensen et al., Eds. (1994) Multi variance analysis—in practice; and, Computer-aided modeling as CAMO, and the Unscrambler's User's guide, Trondheim, Norway, both are incorporated by reference as if fully set forth herein.

It should be noted that such an analysis can be performed on a whole spectral cube. Preferably, the analysis is performed only for selected pixels or mathematically manipulated (e.g., after background subtraction and averaging) selected pixels to improve the results and enable better classification later on. The preferred approach is described in more detail below, nevertheless, there is no intention to limit the scope of the present invention to the preferred approach employed, as different mathematical manipulations may be found useful for different data collection approaches (e.g., filter or dispersion element based spectral imagers).

TRANSMISSION MICROSCOPY

Light microscopy is one of the most fundamental techniques for the visualization of cells and tissues in biology and pathology. Transmission microscopy suffers greatly from the inherently low contrast of cell organelles and structural details. Many methods have been developed to improve this contrast, among them staining and spatial filtering.

In order to facilitate the histological examination of biological specimens, a variety of staining techniques were developed during the last century using organic stains which specifically bind to different macromolecules in the cells, though the molecular basis of the staining techniques has been and still is empirical. The most common staining techniques are the Romanowsky-Giemsa, Haematoxylin-Eosin, mason tricolor and papanicolaou staining.

Whatever the technique, with staining it is possible to distinguish between subcellular compartments of the cell, and especially to distinguish the chromatin organization in the nucleus. Nevertheless, the results obtained from stained specimens remain a matter of experience, art, and subjective interpretation as was published in an editorial by A Bernard Ackerman (1996) entitled "Discordance among expert pathologists in diagnosis of melanocytic neoplasm", in Human pathology 27:1115–1116.

Spectral imaging applied to transmission light microscopy can greatly provide a quantitative measurement of that ratio.

The Romanowsky-Giemsa staining procedure also uses a combination of two dyes, one of which is Azure-B (trimethyl methionine), a thiazin dye, and the second being Eosin Y (hydroxyxanthene bromide). The thiazines are cationic dyes and therefore bind to acidic cellular constituents, whereas Eosin is an anionic dye and tends to bind to basic cellular constituents. It is widely accepted that the use of these two components creates the so-called Romanowsky-Giemsa effect, which is expressed as the development of a specific purple color, a new dye complex, in some stained sites. The molecular basis of the azure-B-Eosin complex is obscure. Some authors think that azure-B binds to anionic structures such as the phosphate groups of DNA, and that Eosin simultaneously binds both with an adjacent cationic site on the DNA and with the azure-B. In a more recently proposed model of the azure-B-Eosin complex, Friedrich and colleagues [Friedrich et al. (1990) Histochemistry 93, pp. 247–256] have suggested that azure-B first binds to phosphodiester residues of the DNA molecule. The authors have hypothesized that the phenyl group of the Eosin molecule is the portion that binds to the azure-B molecule (which lies in a single plane). The color purple is a result of a red shift of the Eosin absorption peak, which in turn is caused by the dielectric polarization of bound Eosin. The very existence of such an azure-B-Eosin complex is still questioned by others [see, Friedrich et al. (1990) Histochemistry 93, pp. 247–256; Bottiroli et al. (1994) Lasers in Surgery and Medicine; Profio (1984) IEEE Journal of Quantum Electronics QE-20 pp. 1502–1506; Herman (1989) Fluorescence Microscopy of Living Cells in Culture, part B, Chapter 8, pp. 219–243, edited by Taylor and Wang, Academic Press Inc.; and, Jovin and Arndt-Jovin (1989) Cell structure and function by microspectrofluorometry, Chapter 5, Academic Press Inc.].

Like Hematoxylin and Eosin, the azure-B and Eosin dyes of the Romanowsky-Giemsa staining are also expected to differentially adhere to cancer as compared to normal cells. Other pairs of dyes (hundreds of dyes are known) may also exhibit similar differential staining characteristics.

Thus, according to the present invention there is provided a method of detecting cancer cells. The method includes the following steps.

First, an analyzed sample suspected as including cancer cells is stained with at least first and second dyes. The dyes are selected such that the first dye better adheres to normal cells present in the sample, whereas the second dye better adheres to cancer cells in the sample.

Second, the sample is spectrally imaged through an optical device optically connected to an imaging spectrometer. Thereby a spectrum of each pixel of the sample is obtained.

Third, based on the spectra obtained, concentrations of the first and second dyes are determined for each of the pixels. The concentrations may be relative concentrations or absolute concentrations.

Finally, based on the concentrations determined, cancer cells in the sample, if any, are detected.

In a prefered embodiment of the present invention the method additionally include a step wherein at least one image indicating the concentrations is presented (e.g., displayed on a computer screen, printed, etc.). Thus, first and second decomposition coefficients maps can be presented (preferably monochromatic maps) as further detailed in the Example given below. Alternatively or additionally a concentration ratios map is presented as further detailed in the Example given below.

According to another preferred embodiment of the present invention the first and second dyes are selected from the pairs of dyes consisting of Hematoxylin and Eosin and thiazin and Eosin.

According to still another preferred embodiment of the present invention the optical device is a microscope.

According to yet another preferred embodiment of the present invention the imaging spectrometer includes an element selected from the group consisting of a dispersion element, a filter and an interferometer. In other words, the method of the present invention can be effected via any device that collects spectral data from a sample in a way that enables (either directly or following mathematical calculations, e.g., Fourier transform) the obtainment of a spectrum for each pixel in the sample. The spectrum may be of high resolution (e.g., 4–10 or 20 nm), medium resolution (e.g., 20–30 nm) or low resolution (e.g., about 50 nm). The spectrum may also be represented by at least two data points obtained using at least two narrow band (e.g., 2–10 nm) filters, as described, for example, in U.S. patent application Ser. No. 08/844,516, which is incorporated by reference as if fully set forth herein, with respect to chromosomes analysis. Thus, as used herein, the term "imaging spectrometer" refers to any multi-band collection device.

Since light transmitance is employed, if a filter is used for spectral imaging, it may be located in any position between the detector array of the imaging spectrometer and the light source of the optical device, either behind or in front of the analyzed sample.

According to another preferred embodiment of the present invention the obtainment of the spectrum of each pixel of step (b) is effected by (i) collecting incident light simultaneously from all pixels of the sample using collimating optics; (ii) passing the incident collimated light through an interferometer system having a number of elements, so that the light is first split into two coherent beams which travel in different directions inside the interferometer and then the two coherent beams recombine to interfere with each other to form an exiting light beam; (iii) passing the exiting light beam through a focusing optical system which focuses the exiting light beam on a detector having a two-dimensional array of detector elements, so that at each instant each of the detector elements is the image of one and always the same pixel of the sample for the entire duration of the measurement, so that the real image of the sample is stationary on the plane of the detector array and at any time during the measurement the image is still visible and recognizable, and so that each of the detector elements produces a signal which is a particular linear combination of light intensity emitted by the pixel at different wavelengths, wherein the linear combination is a function of the instantaneous optical path difference; (iv) scanning one or more of the elements of the interferometer system, so that the optical path difference between the two coherent beams generated by the interferometer system is scanned simultaneously for all the pixels of the sample; and (v) recording signals of each of the detector elements as function of time using a recording device to form a spectral cube of data.

According to another preferred embodiment of the present invention evaluating the concentrations of the first and second dyes for each of the pixels is effected by (i) converting the spectra of the pixels into an absorption spectral image; (ii) obtaining a reference absorption spectrum for each of the first and second dyes; (iii) using the reference absorption spectra for decomposing the absorption spectral image and finding optimal first and second decomposition coefficients; and (iv) using the first and second decomposition coefficients for evaluating the concentrations.

According to yet another preferred embodiment of the present invention converting the spectra of the pixels into an absorption spectral image is effected in accordance with the Lambert Beer law using a background reference spectrum.

According to still another preferred embodiment of the present invention each of the reference absorption spectra is determined by measuring a reference spectrum for each of the dyes and using a background reference spectrum in accordance with the Lambert Beer law for calculating each of the reference absorption spectra.

According to another preferred embodiment of the present invention finding the optimal first and second decomposition coefficients is effected by a minimal square error algorithm.

According to another preferred embodiment of the present invention using the first and second decomposition coefficients for evaluating the concentrations is effected by providing first and second monochromatic coefficients maps for each of the first and second dyes.

According to another preferred embodiment of the present invention a ratio between the concentrations of the dyes for each of the pixels is determined according to the coefficients maps.

According to another preferred embodiment of the present invention a concentration ratios map is provided.

According to another preferred embodiment of the present invention providing the concentration ratios map is effected by an algorithm selected from the group consisting of an RGB algorithm and a classification algorithm.

According to another preferred embodiment of the present invention the concentration ratios map is provided by joining the first and second monochromatic maps, each of the monochromatic maps is of a different monochrome, for obtaining a composite image.

According to another preferred embodiment of the present invention a scatter plot of the ratios is provided.

It will be appreciated by one ordinarily skilled in the art that any cancer cell may be detected using the method of the present invention, including blood cell tumors, such as, but not limited to, leukemia and lymphoma, and solid tumors, such as but not limited to brain tumors, lung tumors, connective tissue tumors, prostate tumors, colon tumors, ovarian tumors, cervical tumors, throat tumors, tumors of the digestive system, skin tumors, and others.

Reference in now made to the following examples, which together with the above descriptions, illustrate the invention.

EXAMPLE

Samples:

Four micron sections of a prostate cancer sample received following prostatectomy and the obtainment of an informed consent from the patient were fixated onto a microscope slide according to well known procedure. The slide was stained in one region thereof with Hematoxylin alone, in another region thereof with Eosin alone and in a third region thereof with both dyes. Staining procedures were as is well accepted in the art.

Spectral Imaging Setup:

The SPECTRACUBE system was connected to a Zeiss Axioskop microscope and the sample was imaged using the × 40 objective lens of the microscope. The illumination source was the standard 50 W Halogen source built into the microscope. One would expect superior results by using a light source which has an emission spectrum that is more balanced over all wavelengths (e.g., Xenon).

The excitation light was conditioned by inserting a KG-1 heat filter in the optical path. This heat filter does not strongly attenuate the near infrared (NIR) light, and, therefore, one would expect better results by inserting a BG-38 or some other NIR blocking heat filter, since the Hematoxylin and Eosin absorptions are in the visible range.

The SPECTRACUBE system was tuned to 8.5 fringes in 100 pixels at 600 nm. All images were captured at step=20 and N=256 frames with an exposure time of 250 ms per frame, such that the total measurement time was about one minute.

Figure 5:
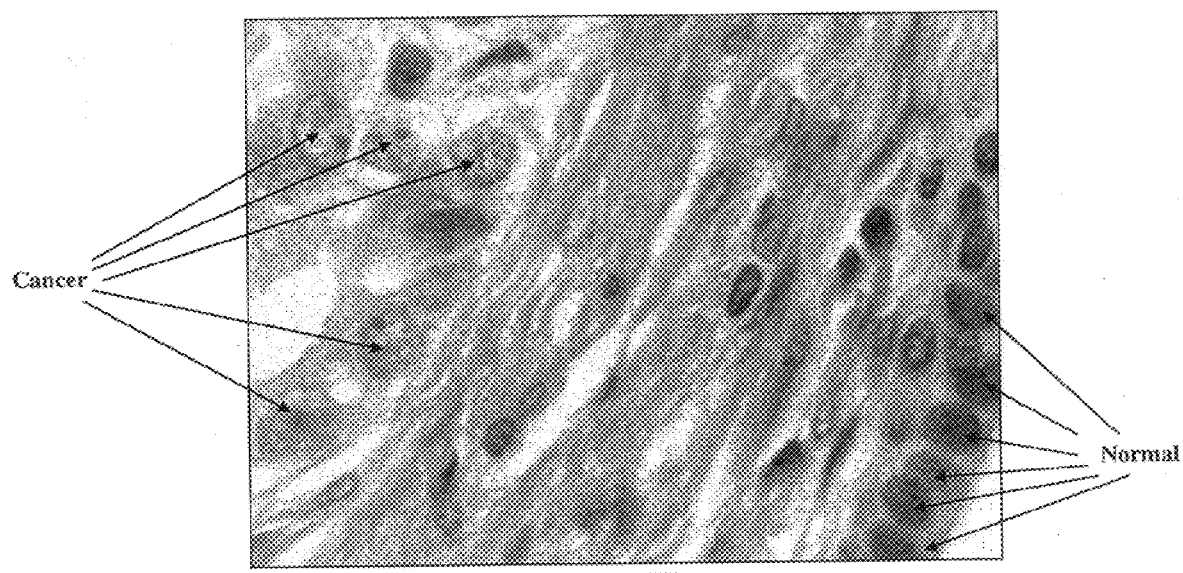
FIG. 5 shows an RGB image of a prostate cancer section stained with both Hematoxylin and Eosin which approximates what is apparent to the eye when views directly through the microscope. The arrows mark cancer and normal cells as was determined by an expert pathologist.

FIG. 5 presents an RGB image (using the RGB algorithm described above) of a prostate cancer section stained with both Hematoxylin and Eosin, which approximates what is apparent to the eye when the sample is viewed directly through the microscope lens. The arrows mark cancer and normal cells as was determined by an expert pathologist.

Measurement of Hematoxylin, Eosin and Background Reference Spectra:

A blank section of the slide was used to measure a background reference spectrum, $B(\lambda)$. When this spectrum, after normalization, was later compared to normalized spectra in regions stained with Hematoxylin and Eosin which appeared to have no absorption it was found to be virtually identical.

A section of the slide stained with only Hematoxylin (H) was imaged to obtain an absorption reference spectrum for Hematoxylin. The Hematoxylin-only spectral image, $H(\lambda)$, was loaded into the SPCUB software program [see, Spectral Images Analysis Manual, by Applied Spectral Imaging Ltd., Migdal Haemek, Israel] and converted into an optical density (OD) image using the background reference spectrum $B(\lambda)$ stored previously in a library. Any other suitable software can be used for such conversion. For convenience, the spectral absorption image was cut and saved in the spectral region from 400 to 750 nm. The reference absorption spectrum for Hematoxylin, $H_{OD}(\lambda)$, was then determined by averaging the absorption spectra (11×11 pixels average) from three selected points in the absorption spectral image which appeared to be the most dense. It was reassuring that the normalized absorption spectrum from virtually all points (not only the most dense points) showed very similar absorption spectra.

In its most simple form, $HOD(\lambda)$ is given by:

$$H_{OD}(\lambda)=\log[H(\lambda)/B(\lambda)] \tag{18}$$

Similarly, a section stained with only Eosin (E) was imaged to obtain an absorption reference spectrum for Eosin. The Eosin-only spectral image, $E(\lambda)$, was loaded into the SPCUB program and converted into an optical density (OD) image using the background reference spectrum $B(\lambda)$ stored previously in the library. For convenience, the spectral absorption image was cut and saved in the spectral region from 400 to 750 nm. The reference absorption spectrum for Eosin, $H_{OD}(\lambda)$, was then determined by averaging the absorption spectra (11×11 pixels average) from three selected points in the absorption spectral image which appeared to be the most dense. Again, it was further reassuring that the normalized absorption spectrum from virtually all points (not only the most dense points) showed very similar absorption spectra.

In its most simple form, $H_{OD}(\lambda)$ is given by:

$$E_{OD}(\lambda)=\log[E(v)/B(\lambda)] \tag{19}$$

Figure 6:
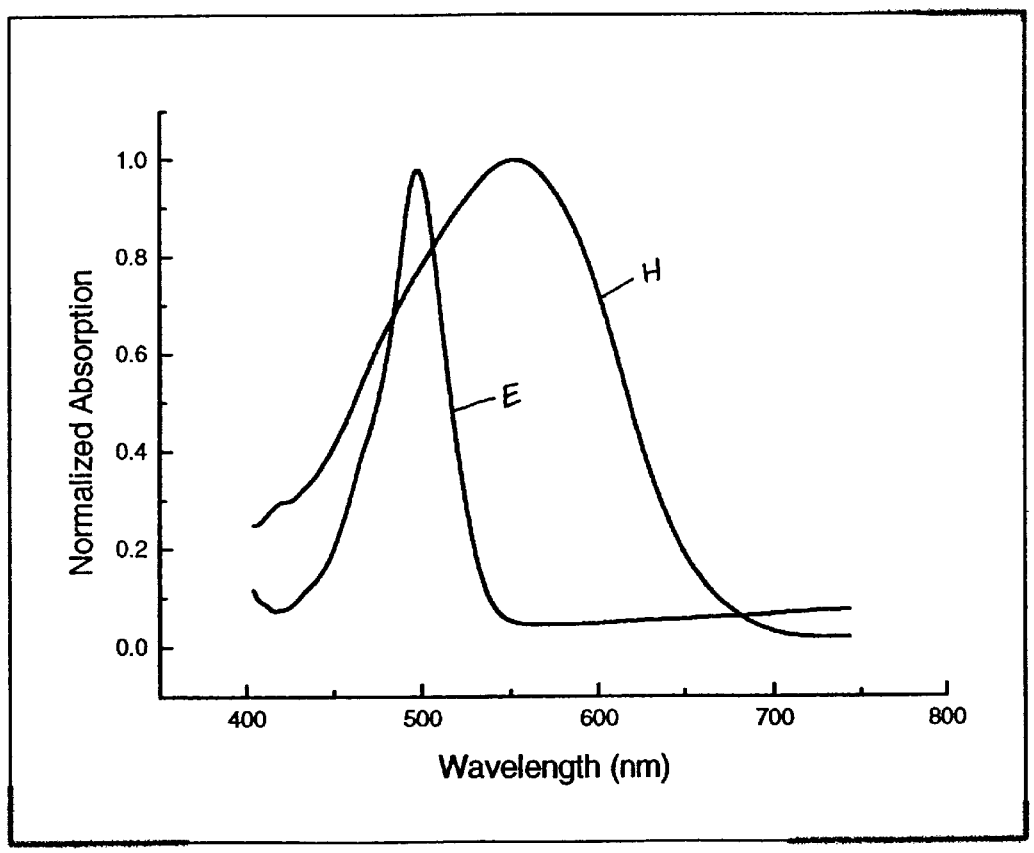
FIG. 6 shows normalized pure stain absorption spectra of Hematoxylin (H) and Eosin (E).

Both pure stain absorption spectra were saved into the library to be used during the spectral decomposition of the Hematoxylin and Eosin images (see below). FIG. 6 shows the normalized pure stain absorption spectra of Hematoxylin (H) and Eosin (E).

Spectral Decomposition:

The four micron thick Hematoxylin and Eosin stained prostate sample was imaged as described above. The spectral image, $H\epsilon E(\lambda)$, was loaded into the SPCUB program and converted into an absorption spectral image (cut from 400 to 750 nm to mask numerical problems) using the background reference spectrum $B(\lambda)$ measured and stored previously in the references library:

$$H\epsilon E_{OD}(\lambda)=\log[H\epsilon E(\lambda)/B(\lambda)] \tag{20}$$

The absorption spectral image, $H\epsilon E_{OD}(\lambda)$, was then decomposed using the absorption reference spectra $H_{OD}(\lambda)$ and $E_{OD}(\lambda)$. To this end, at each pixel (x,y) coefficients a and b were found such that:

$$H\epsilon E_{OD}(\lambda)=aH_{OD}(\lambda)+bE_{OD}(\lambda)+\text{error} \tag{21}$$

Optimum coefficients a and b are, for example, coefficients which minimize the error as determined, for example, using a minimal square error (MSE) algorithm:

$$G_{x,y}^{(1)} = \frac{I_{\max}^2}{40\left(\left(\frac{1}{n}\sum_\lambda (I_{xy}(\lambda)-R_\lambda)^2\right)^{\frac{1}{2}} + \frac{I_{\max}}{40}\right)} \tag{22}$$

(see Equation 2, above)

The output of this algorithm is an image representing values of the a and b decomposition coefficients for each of the pixels. When browsing over pixels through this image one sees two distinct peaks. The right most peak is proportional to the intensity of coefficient a in the linear decomposition, while the left most peak is proportional to the intensity of coefficient b in the linear decomposition.

One can now define ranges that encompass each of these two peaks to view monochrome (e.g., gray level) images showing a(x, y) and b(x, y) for all pixels x,y in the image. The monochrome image with the Hematoxylin concentration is now given by the coefficient map a(x, y) while the monochrome image with the Eosin concentration is given by the coefficient map b(x, y).

Figure 7A:
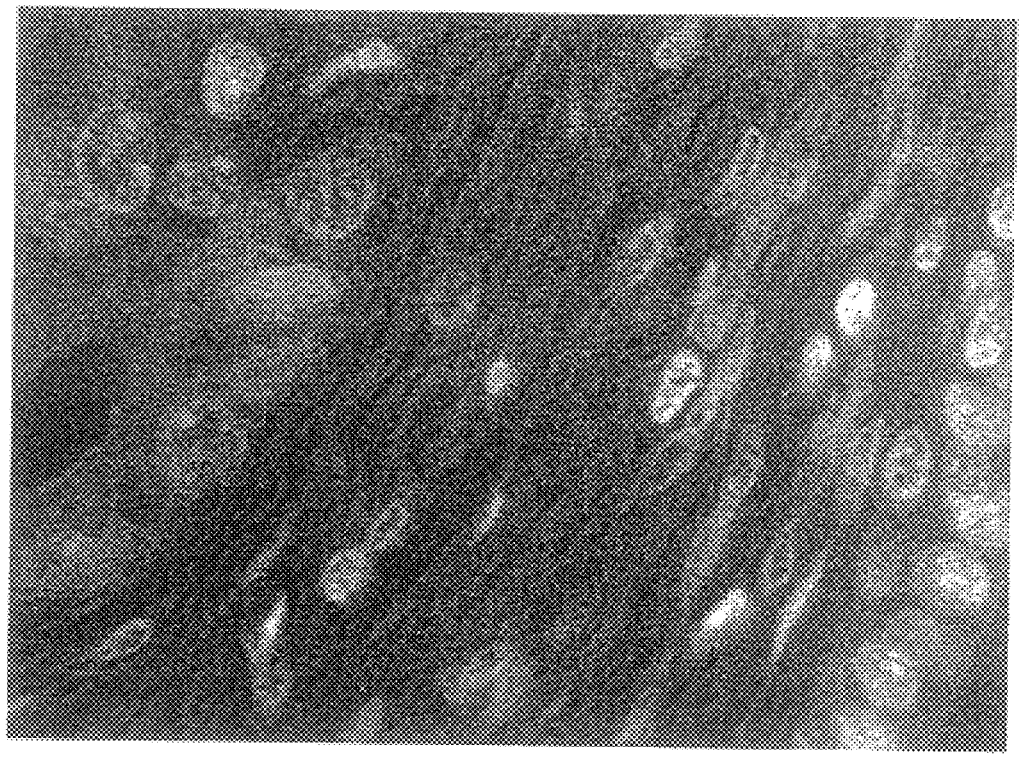
FIGS. 7a and 7b show Hematoxylin and Eosin concentration maps, respectively, of the image of FIG. 6.
Figure 7B:
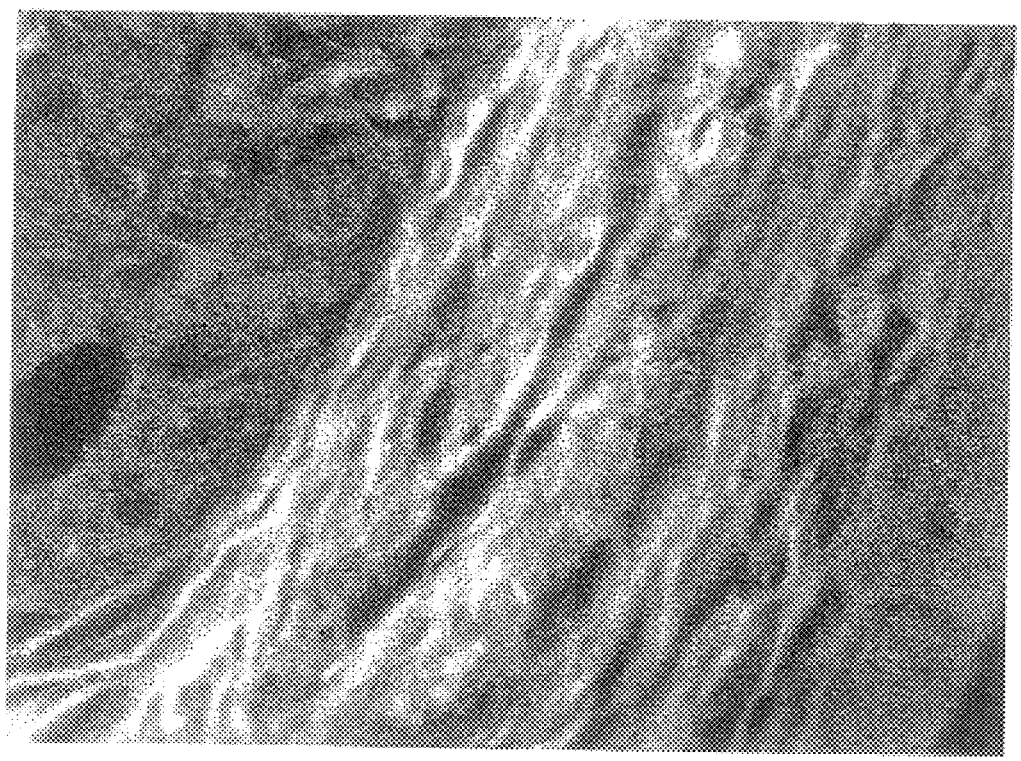
Figure 8A:
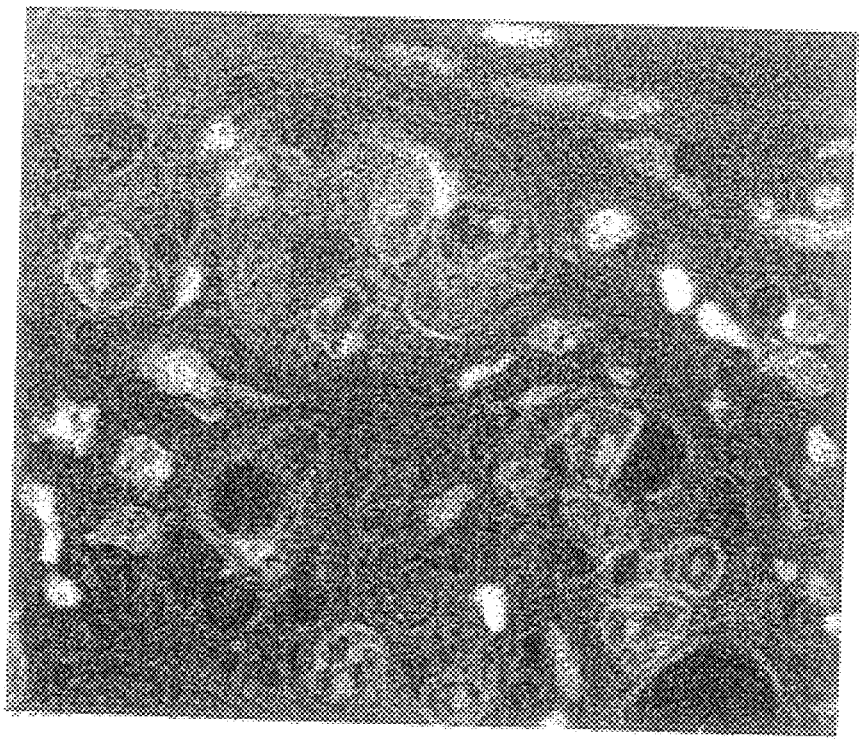
FIGS. 8a–c and 9a–c present Hematoxylin concentration maps, Eosin concentration maps and conventional RGB images, respectively, of two additional sections obtained from the sample presented in FIGS. 6–7.
Figure 8B:
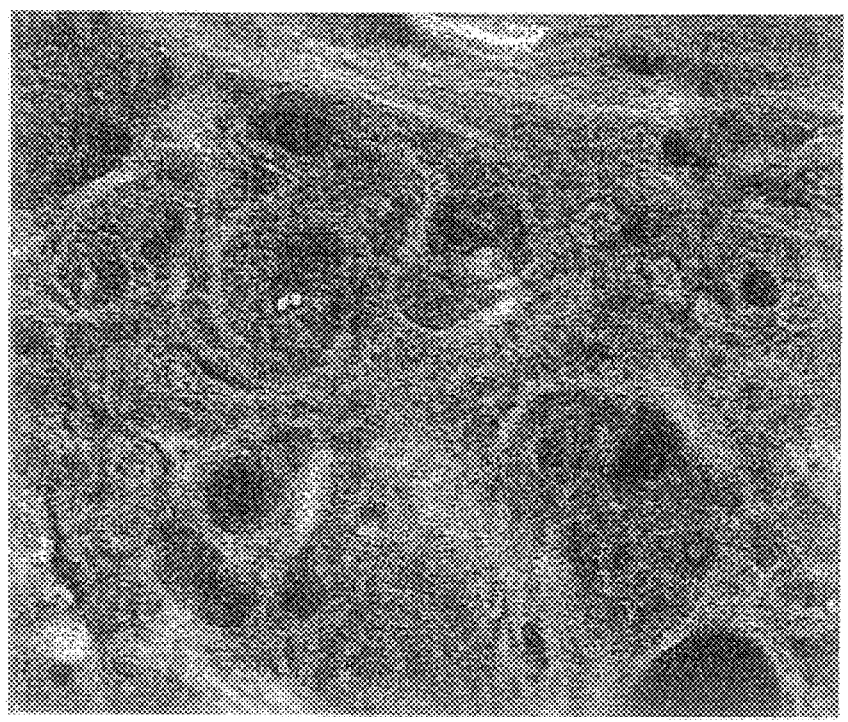
Figure 8C:
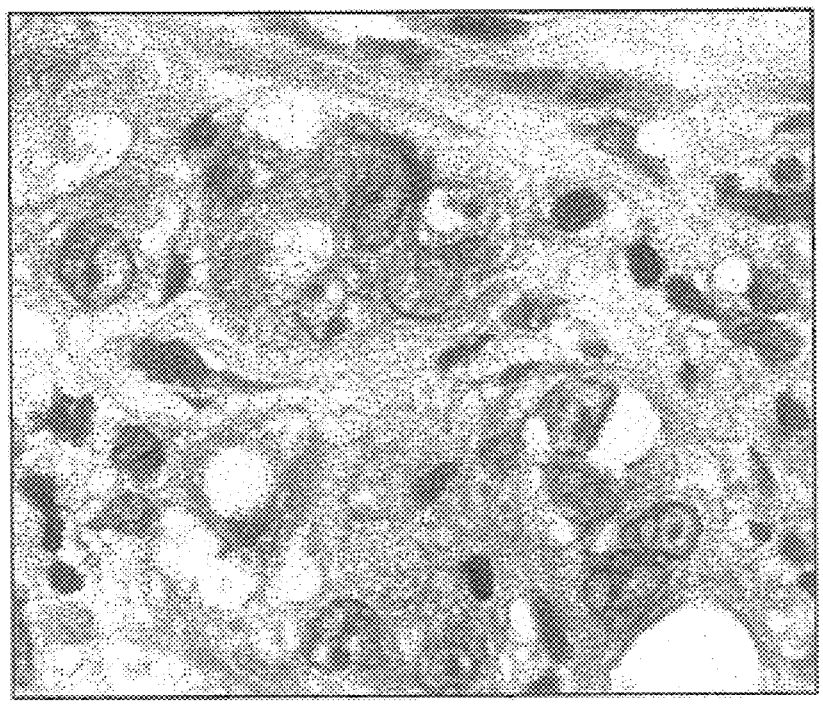
Figure 9A:
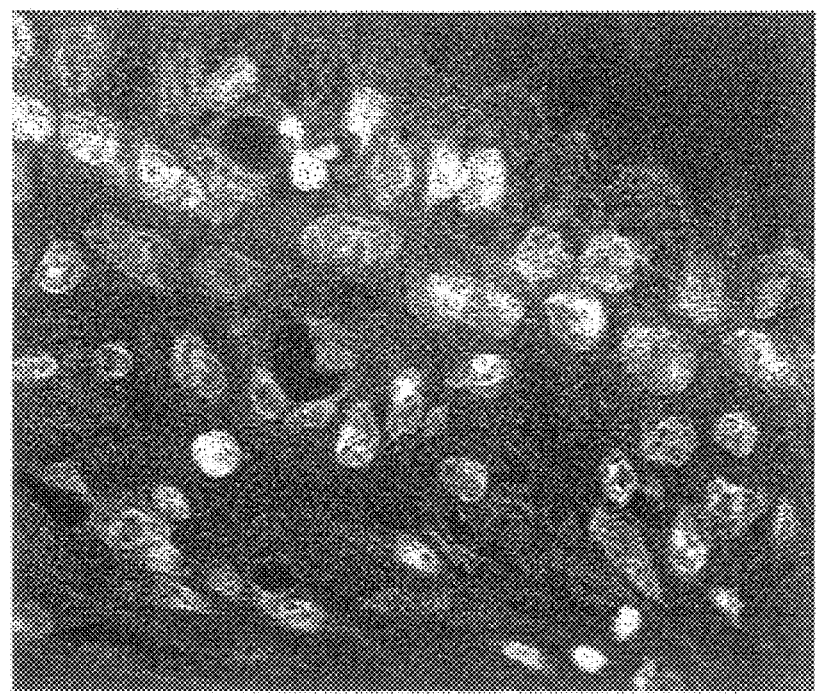
Figure 9B:
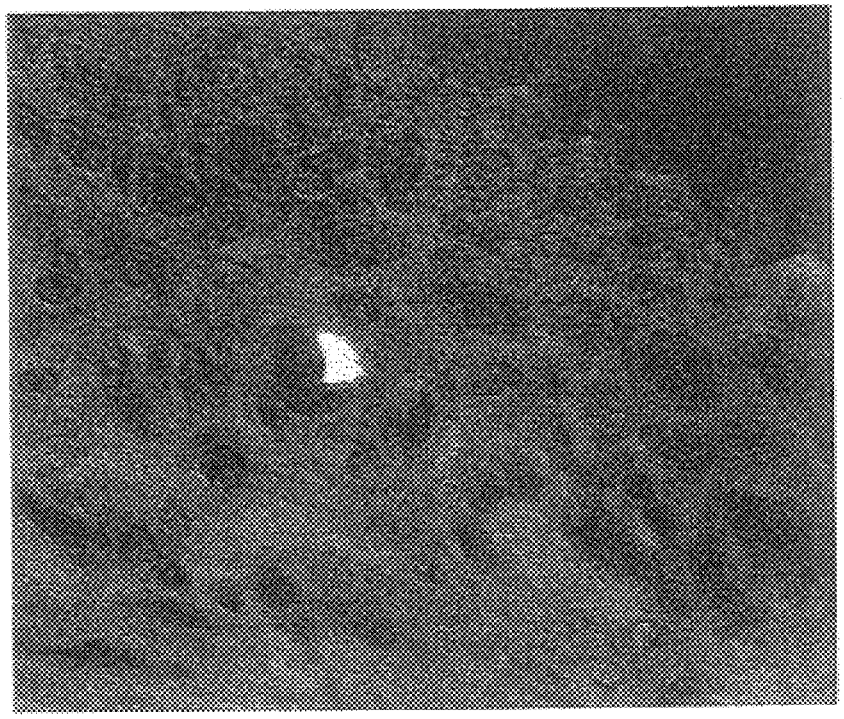
Figure 9C:
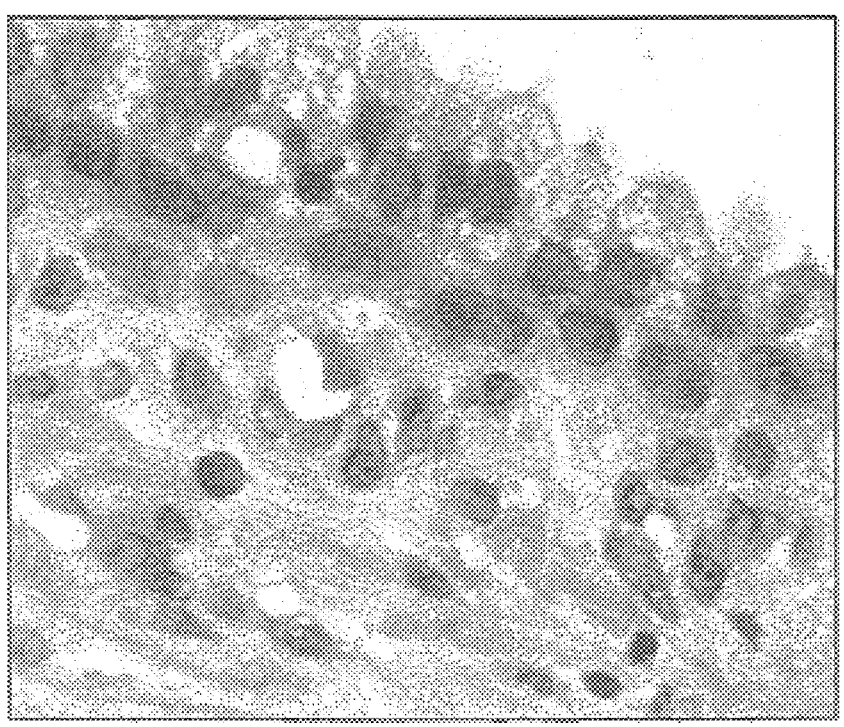

FIGS. 7a and 7b show the Hematoxylin and Eosin concentration maps, respectively, of the image of FIG. 6. Brighter pixels suggest a higher relative concentration of the respective dye, whereas most dark pixels indicate absence of the respective dye.

Please note that Hematoxylin adheres better to normal cells as compared with cancer cells, as indicated by the bright pixels in FIG. 7a.

FIGS. 8a–c and 9a–c present Hematoxylin concentration maps, Eosin concentration maps and conventional RGB images, respectively, of two additional sections obtained from the same sample, wherein the cells were identified as cancer cells.

Please note that in all cases pixels derived from normal cells have a higher ratio of Hematoxylin to Eosin, whereas pixels derived from cancer cells have a lower ratio of Hematoxylin to Eosin.

The analysis of the Hematoxylin and Eosin coefficient maps can take on several forms. One easy thing is to divide Hematoxylin by Eosin (or vice versa), or, in other words, to look at a ratio image given by a(x, y)/b(x, y). Pseudo-coloring such an image by, for example, a suitable RGB algorithm or classification algorithm, can further help in highlighting normal versus cancer cells. One ordinarily skilled in the art would know how to select a suitable RGB algorithm to effect a differentiating pseudo-coloring.

Figure 10:
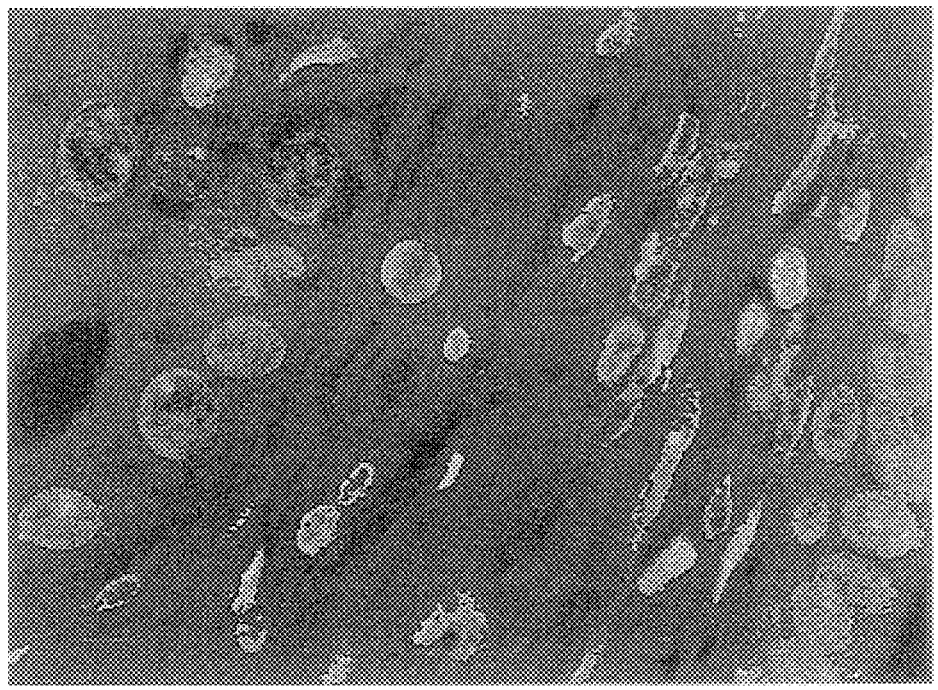
FIG. 10 shows a composite image of the Hematoxylin monochromatic concentration map of FIG. 7a (used in green) and the Eosin monochromatic concentration map of FIG. 7b (used in red).

FIG. 10 presents a simplified form of such an analysis. To construct the color image of FIG. 10 the monochromatic images of FIGS. 7a and 7b were represented in green and red, respectively, and the two monochromatic images were joined to form a composite image, in which normal cells are greenish, as expected from the high Hematoxylin to Eosin ratio characterizing these cells, whereas cancer cells are reddish, as expected from the low Hematoxylin to Eosin ratio characterizing these cells.

A scatter plot, in which for all pixels x,y in the image the value of a (i.e., amount of Hematoxylin) is plotted along the x-axis and the value of b (i.e., amount of Eosin) is plotted along the y-axis, may also prove useful for meaningful presentation of the ratios.

While the invention has been described with respect to a limited number of embodiments, it will be appreciated that many variations, modifications and other applications of the invention may be made.

What is claimed is:

1. A method of detecting cancer cells comprising the steps of:
   (a) staining an analyzed sample with at least first and second dyes, said dyes being selected such that said first dye better adheres to normal cells whereas said second dye better adheres to cancer cells;
   (b) spectrally imaging said sample through an optical device being optically connected to an imaging spectrometer thereby obtaining a full spectrum of each pixel of said sample;
   (c) based on said spectra, evaluating concentrations of said first and second dyes for each of said pixels; and
   (d) based on said concentrations detecting the presence of cancer cells in said sample;
said step of spectrally imaging said sample through said optical device being optically connected to said imaging spectrometer and obtaining said full spectrum of each pixel of said sample allows said at least first and second dyes to be spectrally overlapping.

2. The method of claim 1, further comprising the step of:
   (e) presenting at least one image indicating said concentrations.

3. The method of claim 2, wherein said at least one image includes first and second decomposition coefficients maps.

4. The method of claim 2, wherein said at least one image includes a concentration ratios map.

5. The method of claim 1, wherein said first and second dyes are selected from the pairs of dyes consisting of Hematoxylin and Eosin and thiazin and Eosin.

6. A method of claim 1, wherein said obtainment of said spectrum of each pixel of step (b) is effected by:
   (i) collecting incident light simultaneously from all pixels of said sample using collimating optics;
   (ii) passing said incident collimated light through an interferometer system having a number of elements, so that said light is first split into two coherent beams which travel in different directions inside said interferometer and then said two coherent beams recombine to interfere with each other to form an exiting light beam;
   (iii) passing said exiting light beam through a focusing optical system which focuses said exiting light beam on a detector having a two-dimensional array of detector elements, so that at each instant each of said detector elements is the image of one and always the same pixel of said sample for the entire duration of the measurement, so that the real image of the sample is stationary on the plane of the detector array and at any time during the measurement the image is still visible and recognizable, and so that each of said detector elements produces a signal which is a particular linear combination of light intensity emitted by said pixel at different wavelengths, wherein said linear combination is a function of the instantaneous optical path difference;
   (iv) scanning one or more of said elements of said interferometer system, so that said optical path difference between said two coherent beams generated by said interferometer system is scanned simultaneously for all said pixels of said sample; and
   (v) recording signals of each of said detector elements as function of time using a recording device to form a spectral cube of data.

7. The method of claim 1, wherein said optical device is a microscope.

8. The method of claim 1, wherein said imaging spectrometer includes an element selected from the group consisting of a dispersion element, a filter and an interferometer.

9. The method of claim 1, wherein said evaluation of said concentrations is a relative evaluation.

10. The method of claim 1 wherein said sample is of a prostate.

11. The method of claim 1, wherein evaluating concentrations of said first and second dyes for each of said pixels is effected by:
    (i) converting said spectra of said pixels into an absorption spectral image;
    (ii) obtaining a reference absorption spectrum for each of said first and second dyes;
    (iii) using said reference absorption spectra for decomposing said absorption spectral image and finding optimal first and second decomposition coefficients; and
    (iv) using said first and second decomposition coefficients for evaluating said concentrations.

12. The method of claim 11, wherein converting said spectra of said pixels into an absorption spectral image is effected in accordance with the Lambert Beer law using a background reference spectrum.

13. The method of claim 11, wherein each of said reference absorption spectra is determined by measuring a reference spectrum for each of said dyes and using a background reference spectrum in accordance with the Lambert Beer law for calculating each of said reference absorption spectra.

14. The method of claim 11, wherein finding said optimal first and second decomposition coefficients is effected by a minimal square error algorithm.

15. The method of claim 11, wherein using said first and second decomposition coefficients for evaluating said concentrations is effected by providing first and second monochromatic coefficients maps for each of said first and second dyes.

16. The method of claim 15, further comprising the step of, according to said coefficients maps, determining a ratio between said concentrations of said dyes for each of said pixels.

17. The method of claim 16, further comprising the step of providing a concentration ratios map.

18. The method of claim 17, wherein said concentration ratios map is effected by an algorithm selected from the group consisting of an RGB algorithm and a classification algorithm.

19. The method of claim 17, wherein said concentration ratios map is provided by joining said first and second monochromatic maps, each of said monochromatic maps is of a different monochrome, for obtaining a composite image.

20. The method of claim 16, further comprising the step of providing a scatter plot of said ratios.

* * * * *

UNITED STATES PATENT AND TRADEMARK OFFICE
CERTIFICATE OF CORRECTION

PATENT NO.    : 5,995,645
DATED         : November 30, 1999
INVENTOR(S)   : Dirk C. Soenksen et al.

It is certified that error appears in the above-identified patent and that said Letters Patent is hereby corrected as shown below:

Title page,
After Item [22], insert:
-- Related U.S. Application Data
[63] This is a Continuation-In-Part of U.S. Patent Application No. 08/824,234, filed March 25, 1997, which is a Continuation-In-Part of U.S. Patent Application No. 08/571,047, filed December 12, 1995, now U.S. Patent No. 5,784,162 issued July 21, 1998 which is a Continuation-In-Part of U.S. Patent Application No. 08/392,019 filed February 21, 1995, now U.S. Patent No. 5,539,517, issued July 23, 1996, which is a Continuation-In-Part of U.S. Patent Application No. 08/107,673, filed August 28, 1993, now abandoned. --

Column 1,
Line 3, insert:
-- This application is a Continuation-In-Part of U.S. Patent Application No. 08/824,234, filed March 25, 1997, which is a Continuation-In-Part of U.S. Patent Application No. 08/571,047, filed December 12, 1995, which is a Continuation-In-Part of U.S. Patent Application No. 08/392,019 filed February 21, 1995, now U.S. Patent No. 5,539,517, issued July 23, 1996, which is a Continuation-In-Part of U.S. Patent Application No. 08/107,673, filed August 28, 1993, now abandoned. --

Signed and Sealed this

Sixth Day of May, 2003

JAMES E. ROGAN
*Director of the United States Patent and Trademark Office*